(12) United States Patent
Antaya

(10) Patent No.: US 10,363,435 B2
(45) Date of Patent: *Jul. 30, 2019

(54) CRYOGENIC MAGNET STRUCTURE WITH SPLIT CRYOSTAT

(71) Applicant: Antaya Science & Technology, Hampton, NH (US)

(72) Inventor: Timothy A. Antaya, Hampton Falls, NH (US)

(73) Assignee: Antaya Science & Technology, Hampton, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/882,336

(22) Filed: Jan. 29, 2018

(65) Prior Publication Data

US 2018/0161598 A1 Jun. 14, 2018

Related U.S. Application Data

(63) Continuation of application No. 15/165,750, filed on May 26, 2016, now Pat. No. 9,895,552.

(60) Provisional application No. 62/166,148, filed on May 26, 2015.

(51) Int. Cl.
*A61N 5/10* (2006.01)
*H05H 13/00* (2006.01)
*H01F 6/06* (2006.01)

(52) U.S. Cl.
CPC ............ *A61N 5/1043* (2013.01); *H01F 6/06* (2013.01); *H05H 13/005* (2013.01); *A61N 5/1077* (2013.01); *A61N 2005/1087* (2013.01)

(58) Field of Classification Search
CPC ........ H05H 7/04; H05H 13/00; H05H 13/005; A61N 5/10; A61N 5/1043; A61N 5/1077; H01F 6/00; H01F 6/06
See application file for complete search history.

(56) References Cited

U.S. PATENT DOCUMENTS

| 4,943,781 A * | 7/1990 | Wilson | H05H 13/00 313/62 |
| 6,683,426 B1 * | 1/2004 | Kleeven | H05H 7/10 315/500 |
| 7,541,905 B2 | 6/2009 | Antaya | |
| 7,656,258 B1 * | 2/2010 | Antaya | H01F 6/00 313/62 |

(Continued)

OTHER PUBLICATIONS

USPTO, International Search Report and Written Opinion for PCT/US16/34408 (related PCT application) (dated Sep. 1, 2016).

*Primary Examiner* — Thai Pham
(74) *Attorney, Agent, or Firm* — Modern Times Legal; Robert J. Sayre

(57) ABSTRACT

A cryogenic magnet structure includes at least two superconducting coils, a magnetic yoke, and first and second cryostats. The superconducting coils are substantially symmetric about a central axis, wherein the superconducting coils are on opposite sides of a median plane. The magnetic yoke surrounds the superconducting coils and contains at least a portion of a chamber, wherein the median plane extends through the chamber. The first cryostat contains a first of the superconducting coils, and the second cryostat contains a second of the superconducting coils. The second cryostat is distinct from the first cryostat, and the first and second cryostats are on opposite sides of the median plane in the chamber.

20 Claims, 24 Drawing Sheets

(56) References Cited

U.S. PATENT DOCUMENTS

| | | |
|---|---|---|
| 7,696,847 B2 | 4/2010 | Antaya |
| 7,920,040 B2 | 4/2011 | Antaya et al. |
| 8,111,125 B2 | 2/2012 | Antaya et al. |
| 8,525,447 B2 | 9/2013 | Antaya |
| 8,558,485 B2 * | 10/2013 | Antaya ............... H05H 13/005 315/500 |
| 8,581,525 B2 | 11/2013 | Antaya et al. |
| 8,614,612 B2 | 12/2013 | Antaya et al. |
| 8,975,836 B2 | 3/2015 | Bromberg et al. |
| 9,895,552 B2 | 2/2018 | Antaya |
| 2013/0328475 A1 * | 12/2013 | Hashimoto ......... H05H 13/005 313/47 |
| 2014/0296075 A1 * | 10/2014 | Jongen ............... H05H 13/005 505/163 |
| 2014/0371076 A1 * | 12/2014 | Jongen ................... H05H 7/04 505/200 |
| 2016/0316552 A1 * | 10/2016 | Hashimoto ......... H05H 13/005 |

* cited by examiner

DETAIL A

US 10,363,435 B2

CRYOGENIC MAGNET STRUCTURE WITH SPLIT CRYOSTAT

RELATED APPLICATIONS

This application is a continuation of U.S. application Ser. No. 15/165,750, filed 26 May 2016, the entire contents of which are incorporated herein by reference.

This application also claims the benefit of U.S. Provisional Application No. 62/166,148, filed 26 May 2015, the entire content of which is incorporated herein by reference.

BACKGROUND

A cyclotron for accelerating ions (charged particles) in an outward spiral using an electric field impulse from a pair of electrodes and a magnet structure is disclosed in U.S. Pat. No. 1,948,384 (inventor: Ernest O. Lawrence, patent issued: 1934). Lawrence's accelerator design is now generally referred to as a "classical" cyclotron, wherein the electrodes provide a fixed acceleration frequency, and the magnetic field decreases with increasing radius, providing "weak focusing" for maintaining the vertical phase stability of the orbiting ions.

Among modern cyclotrons, one type is a class characterized as being "isochronous," wherein the acceleration frequency provided by the electrodes is fixed, as with classical cyclotrons, though the magnetic field increases with increasing radius to compensate for relativity; and an axial restoring force is applied during ion acceleration via an azimuthally varying magnetic field component derived from contoured iron pole pieces having a sector periodicity. Most isochronous cyclotrons use resistive magnet technology and operate at magnetic field levels from 1-3 Tesla. Some isochronous cyclotrons use superconducting magnet technology, in which superconducting coils magnetize warm iron poles that provide the guide and focusing fields for ion acceleration. These superconducting isochronous cyclotrons can operate at field levels below 3 Tesla for protons and up to 3-5 Tesla when designed for accelerating heavier ions. The present inventor worked on the first superconducting cyclotron project in the early 1980's at Michigan State University.

Another recent design for an isochronous cyclotron by the present inventor is described in U.S. Pat. No. 8,558,495 B2. This patent describes a compact cold superconducting isochronous cyclotron including superconducting main coils in thermal contact with yoke, where both the main coils and the yoke are maintained at cryogenic temperatures.

Another class of cyclotrons is the synchrocyclotron. Unlike classical cyclotrons or isochronous cyclotrons, the acceleration frequency in a synchrocyclotron decreases as the ion spirals outward. Also unlike isochronous cyclotrons—though like classical cyclotrons—the magnetic field in a synchrocyclotron decreases with increasing radius. Synchrocyclotrons have previously had warm iron poles and cold superconducting coils, like the existing superconducting isochronous cyclotrons, but maintain beam focusing during acceleration in a different manner that scales to higher fields and can accordingly operate with a field of, for example, about 9 Tesla.

SUMMARY

A cryogenic magnet structure and methods for its use in accelerating ions are described herein, where various embodiments of the apparatus and methods may include some or all of the elements, features and steps described below.

A cryogenic magnet structure includes at least two superconducting coils, a magnetic yoke, and first and second cryostats. The superconducting coils are substantially symmetric about a central axis, wherein the superconducting coils are on opposite sides of a median plane. The magnetic yoke surrounds the superconducting coils and contains at least a portion of a chamber, wherein the median plane extends through the chamber. The first cryostat contains a first of the superconducting coils, and the second cryostat contains a second of the superconducting coils. The second cryostat is distinct from the first cryostat, and the first and second cryostats are on opposite sides of the median plane in the chamber.

In particular embodiments, the magnetic yoke is outside the cryostats.

In additional embodiments, at least one cryogenic refrigerator is thermally coupled with the superconducting coils; and an integral maintenance boot assembly can separate the cryogenic refrigerator from the superconducting coil(s) to which it is thermally coupled and can be configured to preserve a vacuum in the cryostats if the cryogenic refrigerator is removed.

In particular embodiments, the magnet structure is a cyclotron; and the cyclotron can have a mass less than 35 tons. Further still, the cyclotron can include a plurality of superconducting flutter coils on each side of the median acceleration plane, a non-magnetic external reinforcement structure, and internal reinforcement structures. Each superconducting flutter coil or pair of superconducting flutter coils serves as a sector pole tip with valleys between the sector pole tips on each side of the median acceleration plane, and the sector pole tips are radially separated across the median acceleration plane by a gap that is narrower than a non-magnetic gap that separates the valleys across the median acceleration plane. The non-magnetic external reinforcement structure fills the valleys between the superconducting flutter coils so as to maintain the positioning of the superconducting flutter coils. The internal reinforcement structures are mounted inside the superconducting flutter coils. The flutter coils on each side of the median acceleration plane can be contained in the respective cryostats.

Additional embodiments in include a voltage source coupled with the superconducting coils to deliver electrical current there through.

The cryogenic magnet structure can further include first and second axial support links. The first axial support link can be coupled with the first superconducting coil and configured to provide a countering force parallel to the central axis to counter an axial magnetic decentering force on the first superconducting coil. The second axial support link can be coupled with the second superconducting coil and configured to provide a countering force parallel to the central axis and opposite to the countering force provided by the first axial support link to counter an axial magnetic decentering force on the second superconducting coil.

In a method for generating a magnetic field for steering an ion beam, at least two superconducting primary coils are cooled to a temperature at least as low as their superconducting transition temperature. The superconducting coils are substantially symmetric about a central axis, are on opposite sides of a median plane, and are surrounded by a magnetic yoke. The cooled temperature of the first superconducting coil is maintained with a first cryostat in which the first superconducting coil is contained, and the cooled temperature of the second superconducting coil is maintained with a second cryostat in which the second superconducting coil is contained. A voltage is provided to the cooled superconducting coils to generate a superconducting current in the superconducting coils; an ion beam is directed across the median plane. The path of the ion beam is then steered with a magnetic field generated by the superconducting coils and the magnetic yoke.

In particular embodiments, the superconducting coils and the magnetic yoke are components of a cyclotron; and the ion beam is introduced in the median plane at an inner radius proximate the central axis. The ion beam is then accelerated in an outward spiral from the inner radius, and the ion beam is extracted from an outer radius after the acceleration. The accelerated ions can reach an energy of 10-250 MeV, and the magnetic yoke can be maintained at a temperature over 200 K as the ion beam is accelerated.

In additional embodiments, the beam of extracted ions are directed at a tumor in a human patient. In a particular embodiment, the beam of extracted ions is scanned across the tumor via pencil beam scanning. The method of claim 11, wherein the ion beam is introduced into the median acceleration plane by injecting the ion beam from an external electron cyclotron resonance ion source.

In particular embodiments, the extracted ions in the beam are protons with an energy of at least 220 MeV. In additional embodiments, the isochronous cyclotron can generates a central magnetic field in the median acceleration plane greater than 3.5 T. Further still, the ion beam can be directed across the median plane in a beam chamber maintained at a temperature between 10° C. and 30° C. between the first and second cryostats.

Figure 1:
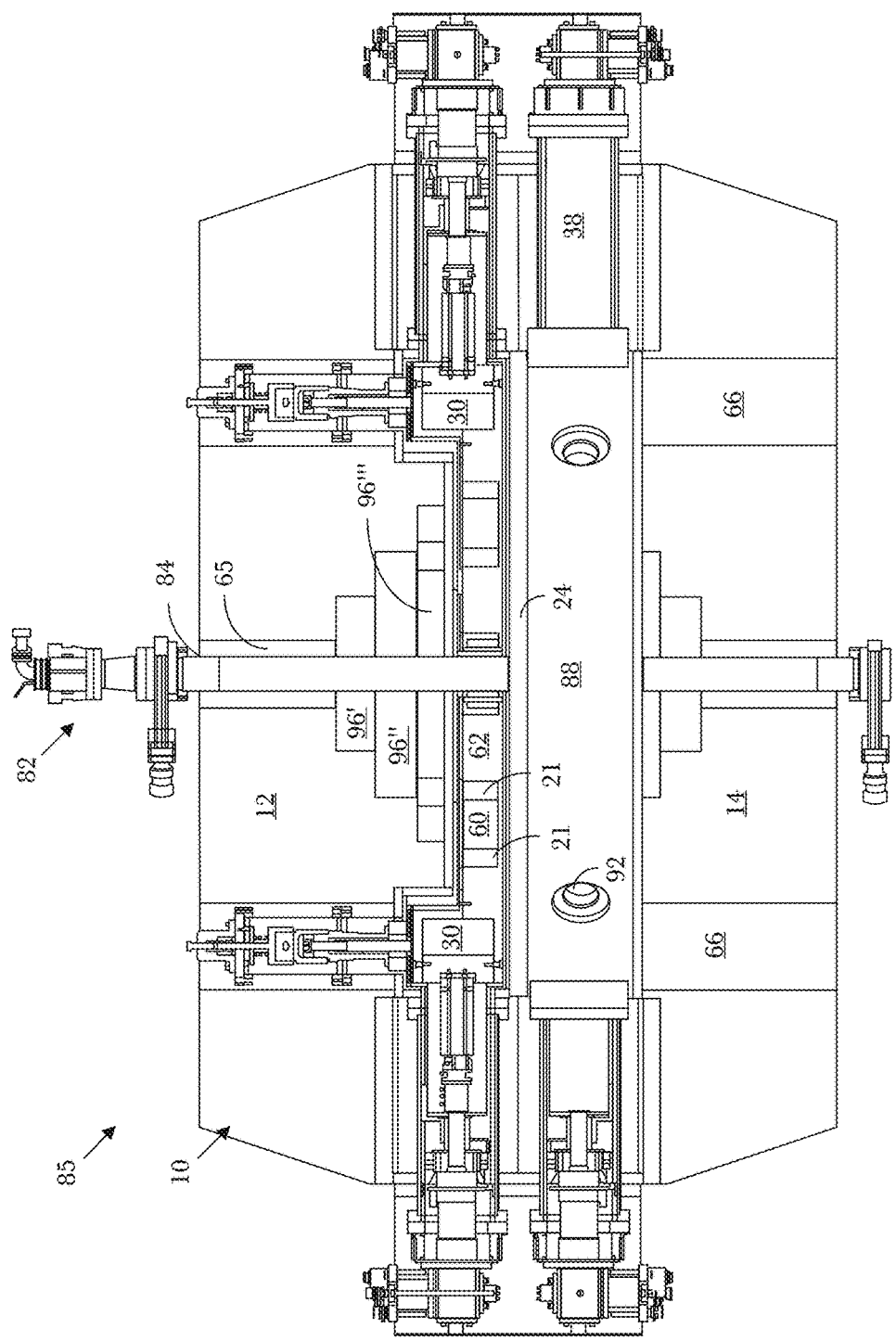
FIG. 1 is a partially sectional side view of an isochronous cyclotron with double cryostats and base plates including superconducting flutter coils 21 embedded in a non-magnetic reinforcement structure 62 within each cryostat.

In the accompanying drawings, like reference characters refer to the same or similar parts throughout the different views; and apostrophes are used to differentiate multiple instances of the same or similar items sharing the same reference numeral. The drawings are not necessarily to scale; instead, emphasis is placed upon illustrating particular principles in the exemplifications discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise herein defined, used or characterized, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume. Processes, procedures and phenomena described below can occur at ambient pressure (e.g., about 50-120 kPa—for example, about 90-110 kPa) and temperature (e.g., −20 to 50° C.—for example, about 10-35° C.) unless otherwise specified.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Additionally, the various components identified herein can be provided in an assembled and finished form; or some or all of the components can be packaged together and marketed as a kit with instructions (e.g., in written, video or audio form) for assembly and/or modification by a customer to produce a finished product.

Index of Terms

The following variables, which are used in the context of isochronous ion acceleration may be referenced in the text that follows:

$B_z$=magnetic field orthogonal to the median acceleration plane 26;
$E_0$=rest mass energy of the ion;
f=magnetic flutter provided by magnetic flutter pole tips;
$f_{rms}$=root mean square of the flutter field;
$F_z$=magnetic force orthogonal to the median acceleration plane 26;
m=mass of ion;
$m_0$=rest mass of ion;
n=field index parameter; in an isochronous cyclotron, $$n = -\frac{r}{B}\left(\frac{dB}{dr}\right) < 0;$$

p=momentum of the ion;
q=charge of ion;
r=radius from central axis 28;
t=time;
T=kinetic energy of accelerated ion;
$V_0$=fixed acceleration voltage;
$V_e$=electrode voltage;
α=momentum compaction of the ion (how momentum changes as a function of radius);
γ(r)=relativistic factor for particle-mass gain with acceleration as a function of radius;
ζ=spiral edge angle;
θ=angular coordinate of the ion about the central axis 28;
$v_z$=oscillation frequency of the accelerated ion orthogonal to the median acceleration plane 26;

$v_r$=radial oscillation frequency of the accelerated ion;
τ=period of rotation of the accelerated ion;
sin φ=sinusoidal voltage when the ion crosses the acceleration gaps (=ωt−θ);
ω=angular velocity of the ion.
N=Isochronous Cyclotron Sector Number that is the number of identical angular magnetic flutter sectors per magnetic pole.

Application of the Isochronous Cyclotron for Proton Therapy

One important application to which the cyclotrons and methods described herein can be applied is for proton therapy provided to cancer patients.

Protons can provide more precise tumor treatment than X-rays can, reducing the overall radiation dose to the patient. In particular, there is no exit dose extending beyond the tumor into normal healthy tissue behind; and there is a significantly lower dose deposited in normal healthy tissue in front of the tumor.

A preferred current mode of proton therapy is pencil-beam scanning where a small diameter proton beam is raster scanned across a tumor layer by layer, from the back of the tumor (highest energy required) to the front of the tumor (a lower energy). Proton beam intensity is lost when the beam is degraded to a lower energy to move up a layer. For a large tumor, this loss may be a factor of a thousand. Because of this intensity loss, the whole treatment takes longer (e.g., tens of seconds to two minutes). When the patient moves during a treatment, the tumor also moves, reducing the positive effect of the high-precision of proton treatments.

Effort is underway to tract tumors and adjust the proton beam path to tract the tumor motion, but this approach will require much technology development and is expected to be very expensive. It would be more advantageous to complete an entire treatment in a single breath hold of the patient via ultra-fast pencil beam scanning (e.g., in about 3-4 seconds) when the tumor is completely at rest. Achieving this speed is believed to require a proton beam intensity that is beyond the capability of known present proton therapy accelerators.

Present-technology continuous-wave (CW) cyclotrons employ a proton-beam generation technology [i.e., internal Penning (or PIG) ion sources in the center of the cyclotron], that is insufficient for ultra-fast pencil-beam scanning. Internal Penning ion sources have refractory cathodes that wear out after a few days of use, requiring cyclotron downtime to replace the used cathodes and to re-tune the cyclotron to restore the proton beam to the high quality and stability required for proton therapy. Internal Penning also presents a gas load in the center of the cyclotron that adversely affects the cyclotron operation and stability—particularly affecting the RF accelerating system that has been used for highly charged, heavy-ion beams [as described in T. A. Antaya, et. al., "The Development of Heavy Ion PIG Sources for the NSCL K-500 Superconducting Cyclotron", 10th Int. Conf Cyclotrons and Their Applications, E. Lansing 126-129 (1984)], as the RF accelerating system may spark and shut down at irregular intervals doe to this gas load. Moreover, PIG ion sources cannot make proton beams of sufficient proton intensity for ultra-fast pencil beam scanning.

The cyclotron design described herein can provide a higher-intensity proton source with an advanced cathode-free confined plasma beam technology, referred to as electron cyclotron resonance (ECR) ion sources 82 to create the initial proton beam injected into the cyclotron 85. The ECR ion source 82 can generate ions predominantly in proton form in a beam with a very small cross-section. No known present-technology cyclotron employs this advanced ion generation technology to produce a proton beam because the source must be external to the cyclotron 85, requiring an injection scheme to deliver the proton beam into the center of the cyclotron 85, where the acceleration begins. Employing the ECR ion source 82 can significantly increase the intensity available for pencil-beam scanning, enabling ultra-fast pencil-beam scanning for the first time, while eliminating cyclotron instability during treatments, down time from RF sparking and cathode replacement maintenance, and subsequent cyclotron retuning to produce high-quality proton beams for proton therapy treatments.

Present-technology CW isochronous cyclotrons, whether comprising resistive magnets or superconducting magnets, may be limited to magnetic fields of less than 3 Tesla. This comparatively low magnetic-field magnitude makes the cyclotrons large and expensive. As a consequence, there are few total systems relative to need; and less than 5% of cancer patients have access to them.

CW isochronous cyclotrons have protons that exit the cyclotron on every RF cycle (many million times per second) providing for a layer scan of a few milliseconds that will repaint the layer with more than a thousand small-intensity pulses from the cyclotron. This repetition assures that the tumor is repainted many times with the beam to insure that no part of the tumor on this layer is missed during this layer scan.

In general, pencil-beam scanning cannot be done easily with low-intensity, low-duty fact synchrocyclotrons, even with high-field compact superconducting cyclotrons. Ultra-fast pencil beam scanning is completely prohibited with these devices. Existing synchrocyclotrons also employ internal Penning ion sources to create the initial proton beam, with all of the associated adverse effects.

CW Isochronous cyclotrons may be made smaller and less expensive. Doubling the operating magnetic field level from 2 Tesla to 4 Tesla reduces the cost by a factor of three, and this cost-reduction would significantly improve the availability of this life-saving precision treatment to more cancer patients.

The CW isochronous cyclotron can be made more compact via the following three achievements: (1) providing the magnetic field with the correct radial profile to achieve isochronous acceleration from the center to the radius at which the final energy is to be achieved; (2) providing the magnetic field with the correct axial distribution, referred to as "flutter," which is an azimuthal variation of the magnetic field, in the beam chamber 24 to provide axial beam stability over the full acceleration; and (3) providing a sufficient gap in the beam chamber 24 to permit the installation and operation of a set of RF acceleration structures of sufficient time-varying voltage and frequency to accelerate the protons from low energy in the cyclotron center to full energy at the final radius. In addition, proton therapy utilizes a final proton energy of at least 230 MeV, corresponding to a proton range of 20 cm in water, a depth considered to be necessary to reach tumors in the interior of an average human, where the human comprises mostly water, to achieve the intensity level required for next-generation ultra-fast pencil beam scanning, to treat an entire large tumor, back to front, in multiple scanned layers, a high-intensity proton beam is injected into the cyclotron 85 from an external ECR ion source 82.

In known present-generation cyclotrons, this set of three fundamental and simultaneous cyclotron requirements plus the required final energy for proton therapy, has not been achieved for a CW isochronous proton cyclotron with a central field greater than about 2.5 T. As a consequence, these cyclotrons are large and cannot practically be transported in an assembled state; and they are heavy (e.g., 100 tons to 250 tons or 90,700 kg to 226,800 kg). These cyclotrons also are too expensive for widespread deployment in virtually any community, unlike the present generation of (inferior) X-ray treatment systems.

No known present-technology CW isochronous cyclotron for proton therapy is configured to permit high-intensity proton beam injection from a cathode-free external ECR ion source 82.

Isochronous cyclotrons 85 described herein can simultaneously solve all five of these requirements for ultra-fast pencil beam scanning in a 230 MeV CW isochronous cyclotron 85 with a central field greater than 4 T and a mass less than 35 tonnes, resulting in a compact low-cost system with an overall envelope sufficiently small enough that it that may be transported fully assembled essentially anywhere and deployed in virtually any community, similar to the deployment of existing X-ray treatment systems. Because people who require treatment may be quite sick, providing a fast, accurate, low-cost, superior treatment in their home community can be highly beneficial.

Design of the Isochronous Cyclotron

Embodiments of an isochronous cyclotron 85 are shown in the FIGS. 1-3 and 6-12 from various perspectives and via sections. As shown in FIGS. 3 and 8-10, the isochronous cyclotron 85 includes superconducting primary coils 30 and 32; a magnetic yoke 10, including a pair of poles 12 and 14 and a return yoke 22; a base plate 13, including a plurality of superconducting spiral-shaped flutter coils 21 (e.g., having edges that follow the path of an Archimedes spiral with a spiral constant of 2); a non-magnetic external reinforcement structure 62 surrounding the flutter coils 21; and internal reinforcement structures 60 inside the flutter coils 21. The yoke 10 contains at least a portion of a beam chamber 24 through which passes a median acceleration plane 26 for ion acceleration. The poles 12 and 14 exhibit approximate mirror symmetry across the median acceleration plane 26 and are joined at the perimeter of the magnetic yoke 10 by the return yoke 22. Cut-outs 96 in the yoke 10 around the central axis 28 provide field shaping for the magnetic field profile required for isochronous ion acceleration in the cyclotron 85.

Figure 13:
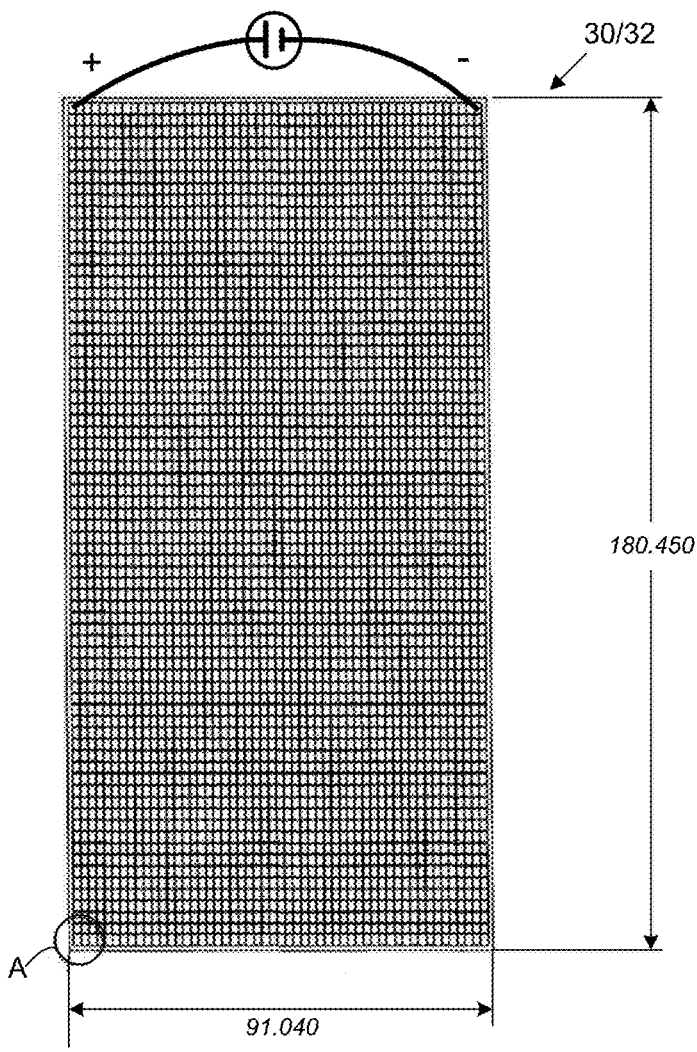
FIG. 13 is a sectional view of a primary coil 30/32.
Figure 14:
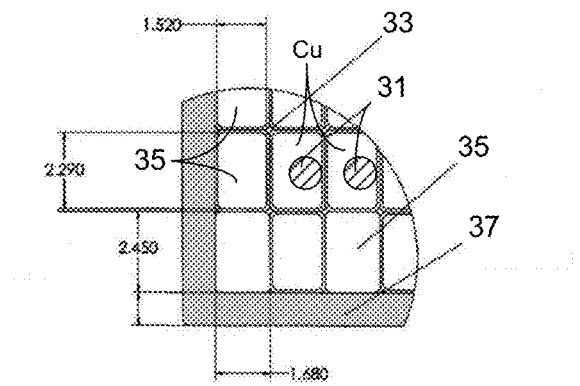
FIG. 14 is a magnified view of a section of the coil 30/32 from FIG. 13.

The pair of superconducting primary coils 30 and 32 generate a magnetic field in the beam chamber 24 and are positioned on opposite sides of the median acceleration plane 26 and encircle a central axis 28 at their center. Sectional views of the superconducting primary coils 30 and 32 are shown in FIGS. 13 and 14, where FIG. 14 is a magnified view of the indicated section of FIG. 13. As shown in FIG. 14, the windings 31 of the primary coil 30/32 are separated by S2 glass insulation; and the outer windings 31 of the superconductor wire are surrounded by spacers 35 that fill gaps at the perimeter that are produced by the winding process; and a ground wrap 37 surrounds the spacers 35 at the perimeter. Each superconductor wire is encased in a U-shaped conductive (e.g., copper) channel that can carry the current flow if and when the superconductor reaches a normal (non-superconducting) temperature during operation (e.g., due to a loss of vacuum in the cryostat 56). The primary coils 30 and 32 are designed to have a high inductance (e.g., the inductance of the coil, $L_{coil}$, can be greater than 30 H). In particular embodiments, the primary coils 30 and 32 can each have 27 columns of windings 31 (counted horizontally in the image of FIG. 13) and 71 rows (counted vertically in the image of FIG. 13) of windings 31; and each primary coil 30/32 can be spaced 57 mm from the median acceleration plane 26.

The superconducting primary coils 30 and 32 are supplied with electric current via a low-temperature conductive electric current lead coupled with a voltage source, as discussed infra. Meanwhile, cryogenic cooling is provided via cryocoolers 38 fed through cutouts 94 in the section 88 of the cryostat 56 covering the bobbin 11 and bolted to the bobbin 11 at the end of the second stage 52 of the cryocooler 38, as shown, e.g., in FIGS. 9 and 10, and delivered to the primary coils 30 and 32 to cryogenically cool the coils 30 and 32 to below their critical temperature and to likewise cool the bobbin 11 and the base plate 13, including the superconducting flutter coils 21. As shown in FIGS. 8-12, the bobbin 11 surrounds and is flush with both the primary coil 30/32 and with the non-magnetic external reinforcement structure 62 to provide mechanical support and containment. The bobbin 11 can be formed, e.g., of aluminum. Exemplary dimensions of the base plate 13, superconducting primary coil 30 and bobbin 11 are shown (in millimeters) in FIG. 11, which is a sectional side view taken along section A-A, shown in FIG. 12.

Partially schematic sectional illustrations of the primary coils 30 and 32 are provided in FIGS. 13 and 14. In one embodiment, a single-strand cable can carry 100-400 amperes and provide about a million amps-turns. In general, the coil can be designed with as many windings 31 (e.g., 3,816 windings) as are needed to produce the number of amps-turns needed for a desired magnetic field level without exceeding the critical current carrying capacity of the superconducting strand. The superconducting material can be a low-temperature superconductor, such as niobium titanium (NbTi), niobium tin ($Nb_3Sn$), or niobium aluminum ($Nb_3Al$); in particular embodiments, the superconducting material is a type II superconductor—in particular, $Nb_3Sn$ having a type A15 crystal structure. High-temperature superconductors, such as $Ba_2Sr_2Ca_1Cu_2O_8$, $Ba_2Sr_2Ca_2Cu_3O_{10}$, $MgB_2$ or $YBa_2Cu_3O_{7-x}$, can also be used.

The primary coils 30 and 32 can be formed directly from a superconducting wire or a superconducting-wire-in-channel conductor. In the case of niobium tin ($Nb_3Sn$), unreacted strands of niobium and tin (in a 3:1 molar ratio) can also be wound into cables. The cables are then heated to a temperature of about 650° C. to react the niobium and tin to form $Nb_3Sn$. The $Nb_3Sn$ cables are then soldered into a U-shaped copper channel to form a composite conductor. The copper channel provides mechanical support, thermal stability during quench, and a conductive pathway for the current when the superconducting material is normal (i.e., not superconducting). The composite conductor is then wrapped in glass fibers and then wound in an outward overlay. Strip heaters formed, e.g., of stainless steel can also be inserted between wound layers of the composite conductor to provide for rapid heating when the magnet is quenched and also to provide for temperature balancing across the radial cross-section of the coil after a quench has occurred, to minimize thermal and mechanical stresses that may damage the coils. After winding, a vacuum is applied, and the wound composite conductor structure is impregnated with epoxy to form a fiber/epoxy composite filler in the final coil structure. The resultant epoxy-glass composite in which the wound composite conductor is embedded provides electrical insulation and mechanical rigidity. Features of embodiments of primary coils 30 and 32 and their construction are further described and illustrated in U.S. Pat. No. 7,696,847 B2 and in U.S. Pat. No. 7,920,040 B2.

In other embodiments, the primary coils 30 and 32 can be formed of individual strands (small round wires) and wet wound with epoxy then cured, or dry wound and impregnated after winding to form a composite coil.

Each primary coil 30/32 can be covered by a ground-wrap additional outer layer of epoxy-glass composite and a thermal overwrap of tape-foil sheets formed, e.g., of copper or aluminum, as described in U.S. Pat. No. 8,525,447 B2; and each primary coil 30/32 is thermally and physically coupled with the second stage 52 of at least one cryocooler 38.

The superconducting primary coils 30 and 32 circumscribe the region of the beam chamber 24 in which the ions are accelerated, on opposite sides of the median acceleration plane 26 and serve to directly generate extremely high magnetic fields in the median acceleration plane 26. When activated via an applied voltage, the superconducting primary coils 30 and 32 further magnetize the yoke 10 so that the yoke 10 also produces a magnetic field, which can be viewed as being distinct from the field directly generated by the superconducting primary coils 30 and 32.

The superconducting primary coils 30 and 32 are substantially (azimuthally) symmetrically arranged about the central axis 28 equidistant above and below the median acceleration plane 26 across which the ions are accelerated. The superconducting primary coils 30 and 32 are separated by a sufficient distance to allow for radiofrequency (RF) acceleration electrode dees 40 to extend there between in the beam chamber 24, inside of which a temperature at or near room temperature (e.g., about 10° C. to about 30° C.) can be maintained.

Figure 6:
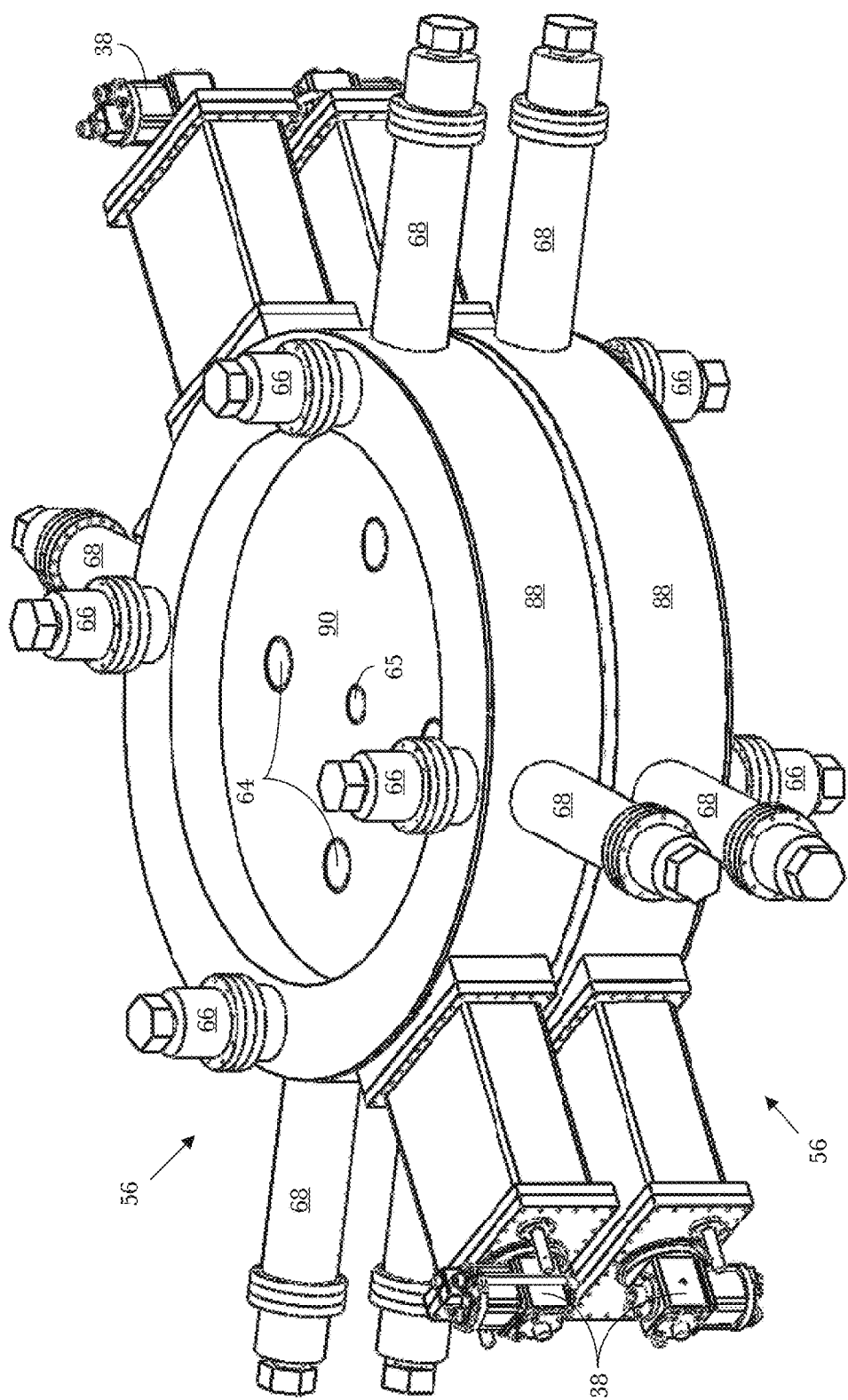
FIG. 6 is a perspective view of a double-cryostat structure in a isochronous cyclotron, each cryostat 56 including a bobbin containing a base plate that contains superconducting flutter coils contained in an aluminum support structure.
Figure 7:
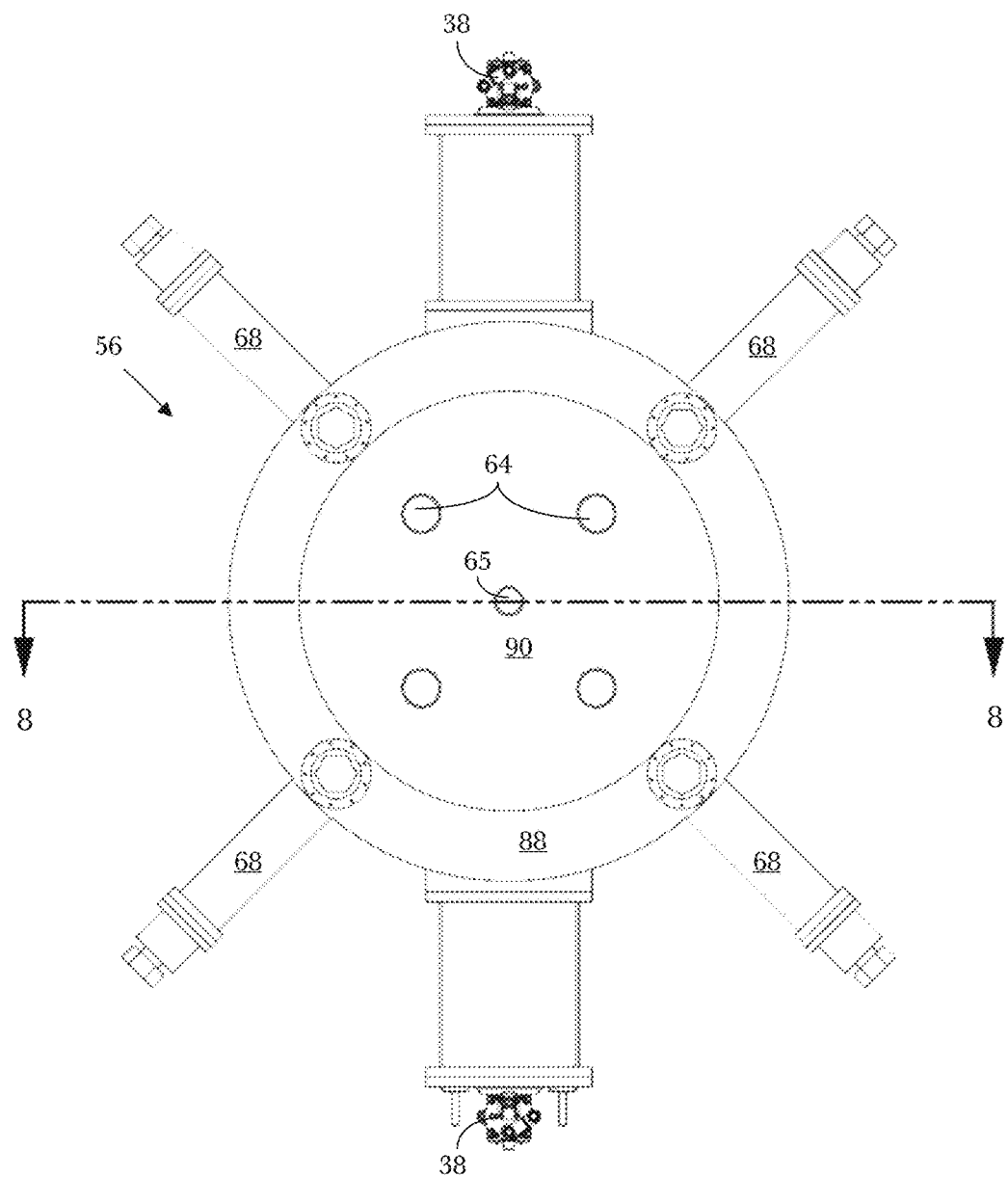
FIG. 7 is a top view of the top section 90 of the cryostat 56 of FIG. 6, showing the section plane, illustrated in FIG. 8.
Figure 8:
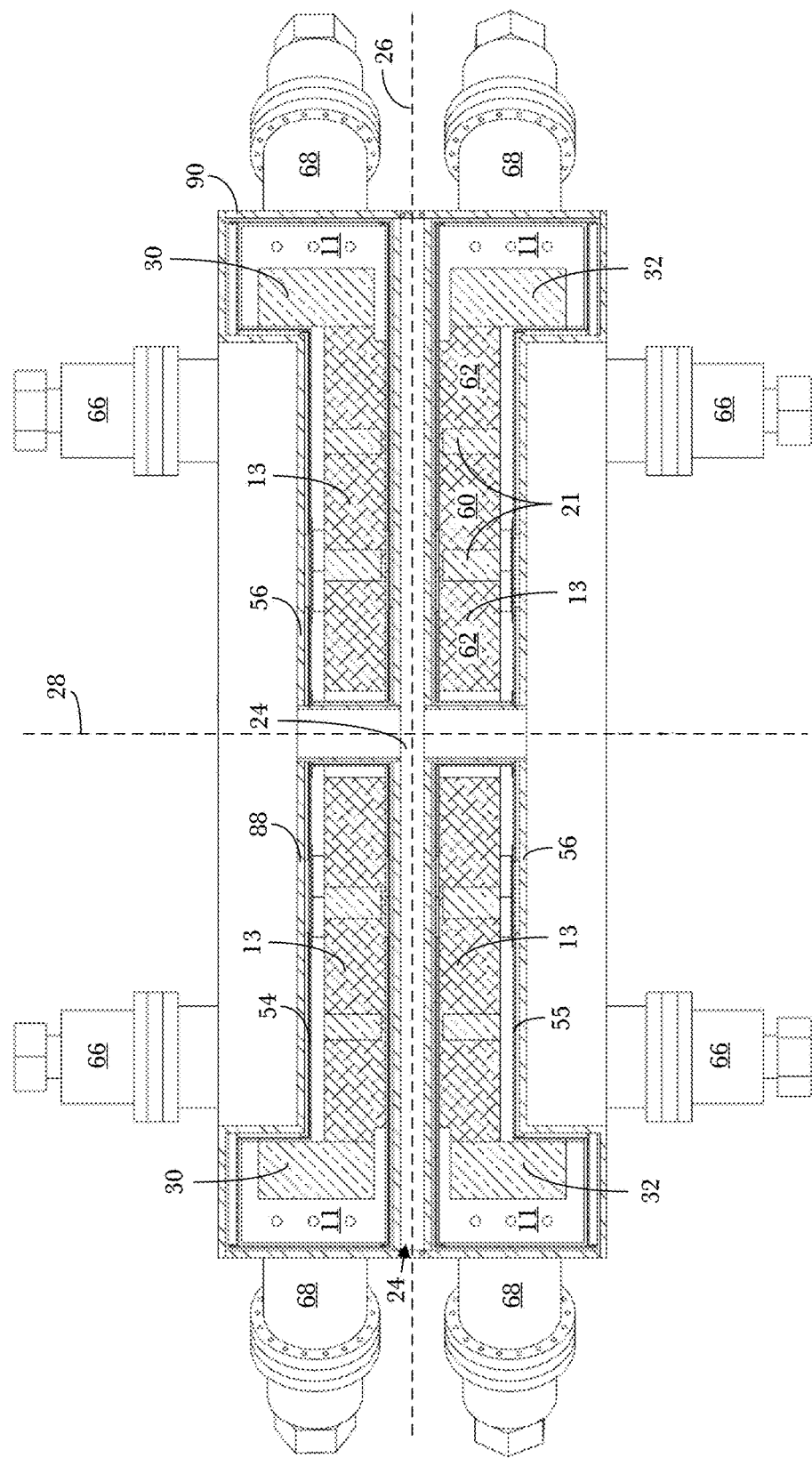
FIG. 8 is a side sectional view, taken along the section 8-8 shown in FIG. 7, showing the double cryostat 56 containing the base plate 13 (with the superconducting flutter coils 21 and a conforming aluminum support structure) and the superconducting coils and bobbin 11.

The primary coils 30 and 32 can be contained in separate cryostats 56 (including sections 88 and 90), as shown in FIGS. 6-8; or a single cryostat 56 can encompass the entire magnet structure with a warm, insulated penetrating enclosure designed for the electrodes and beam chamber 24. Each of the superconducting primary coils 30 and 32 includes a continuous path of conductor material that is superconducting at the designed operating temperature, generally in the range of 4-40K, but also may be operated below 2K, where additional superconducting performance and margin is available. Where the cyclotron 85 is to be operated at higher temperatures, superconductors, such as bismuth strontium calcium copper oxide (BSCCO), yttrium barium copper oxide (YBCO) or $MgB_2$, can be used.

The non-magnetic external reinforcement structure 62 can be machine cut from a solid plate, of, e.g., aluminum, to produce spiral-shaped apertures that have substantially the same shape as the flutter coils 21, though the spiral-shaped apertures of the non-magnetic external reinforcement structure 62 are slightly larger than the perimeter of the flutter coils 21 at room temperature (e.g., around 25° C.) to produce a void/gap between the non-magnetic external reinforcement structure 62 and the flutter coils 21 at room temperature. Similarly, the internal reinforcement structures 60 (formed, e.g., of copper or stainless steel) have substantially the same shape as the flutter coils 21, though the spiral-shaped internal reinforcement structures 60 are slightly smaller than the internal surfaces of the flutter coils 21 at room temperature to likewise leave a gap between each internal reinforcement structure 60 and the flutter coil 21 in which it is contained at room temperature. The sizes of the room-temperature gaps control the stress state of the flutter coils 21 and are established to ensure that the superconducting flutter coils 21 operate as intended.

When the cryocoolers 38 are activated, heat is extracted from the flutter coils 21 through the non-magnetic external reinforcement structure 62 and through the bobbin 11 to the cryocoolers 38, thereby dropping the temperature of the flutter coils 21 below their critical temperatures at which they become superconducting. The non-magnetic external reinforcement structure 62 and the internal reinforcement structures 60 are cooled simultaneously with the flutter coils 21; and the non-magnetic external reinforcement structure 62 is structured to contract more with decreasing temperature than does the flutter coil 21, while the flutter coil 21 is structured to contract more with decreasing temperature than does the internal reinforcement structure 60. Consequently, when these components drop below the critical temperature (e.g., 4 k), each flutter coil 21 is in flush contact about its outer perimeter with the non-magnetic external reinforcement structure 62 and is in flush contact along its inner perimeter with the internal reinforcement structure 60 to thereby secure, contain and support the flutter coils 21 to maintain the position and structural integrity of the flutter coils 21 inside the yoke 10.

Figure 15:
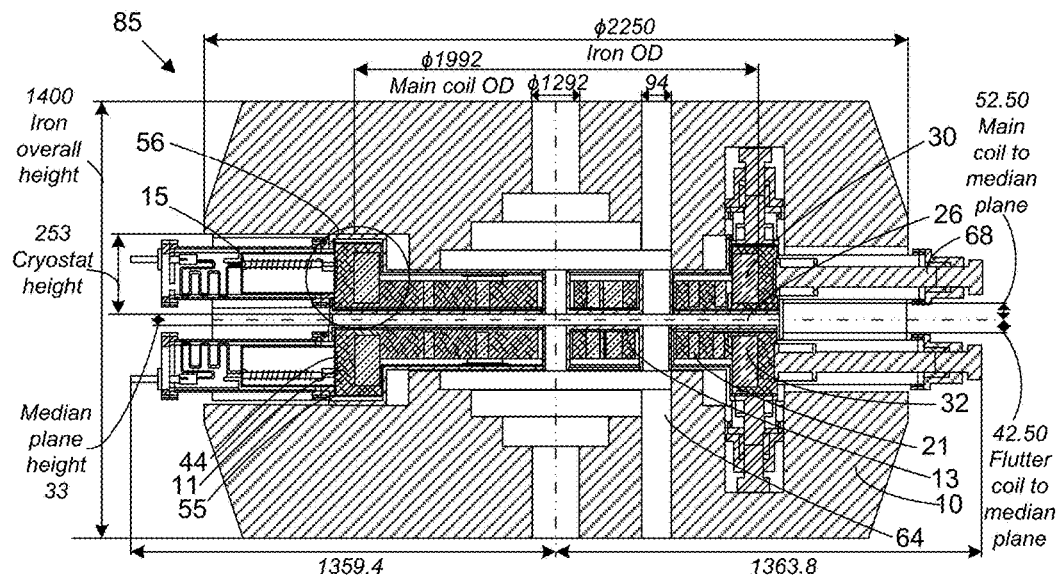
FIG. 15 is a sectional view of an embodiment of the isochronous cyclotron 85 (indicated dimensions are in mm, here and in the other Figures).
Figure 16:
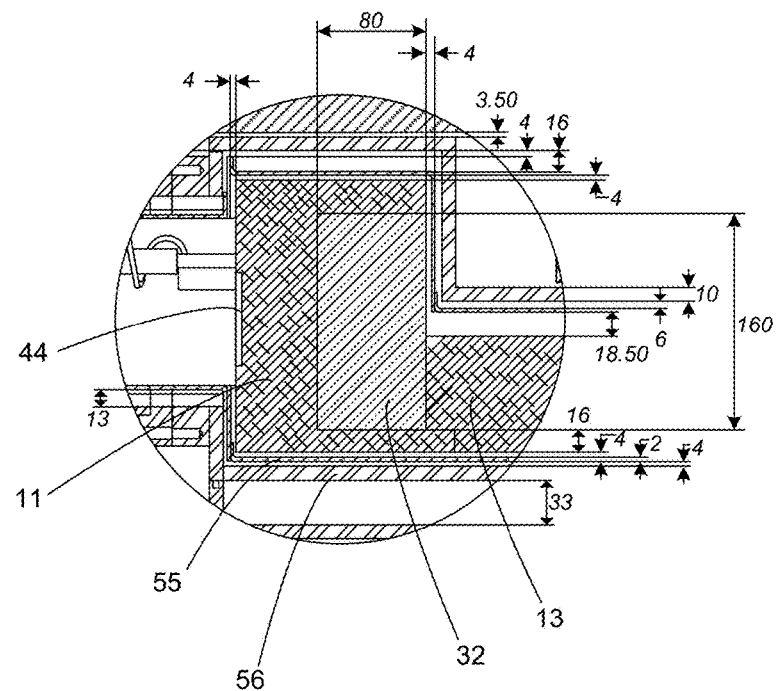
FIG. 16 is a magnified view of the encircled section from FIG. 15.
Figure 17:
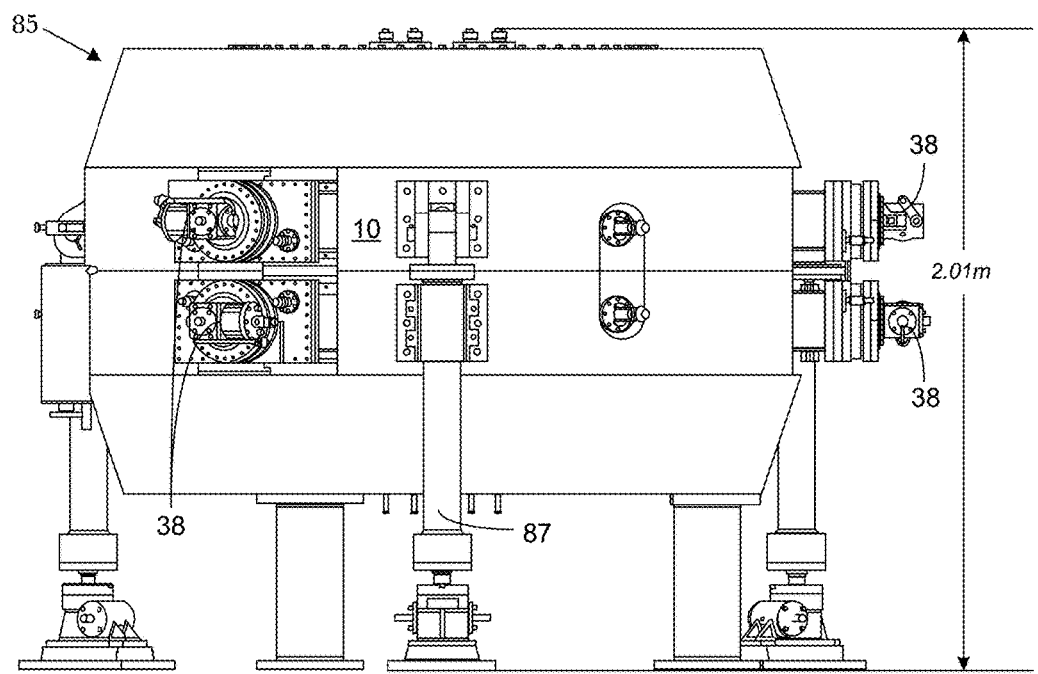
FIG. 17 is a side view of an embodiment of the isochronous cyclotron.
Figure 18:
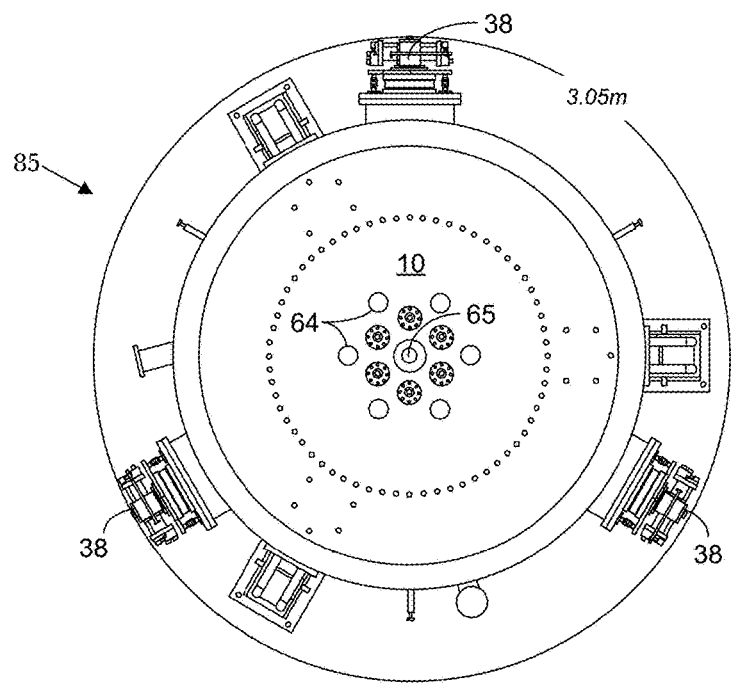
FIG. 18 is a top view of the isochronous cyclotron of FIG. 17.

A sectional view of an isochronous cyclotron 85 is shown in FIGS. 15 and 16, showing the high-temperature lead 23 into the cryostat 56 and the bobbin 11, cold-head port 44, heat shield 55, and base plate 13 about the primary coils 30 and 32. Also shown are the yoke 10, RF lead channels 64, and radial support links 68. Side and top views of the cyclotron 85, with the jacking system 87 and configuration of three cryocoolers 38 for enhanced cooling of a three-sector flutter-coil structure, are respectively shown in FIGS. 17 and 18.

Figures 28, 29:
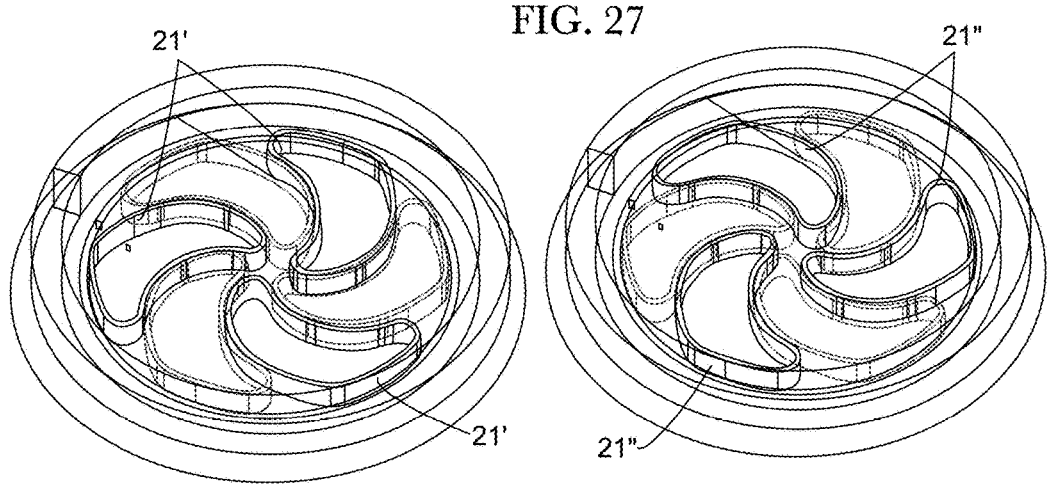
FIGS. 28 and 29 shows a three-sector, six-flutter-coil configuration for an embodiment of the isochronous cyclotron.
Figure 39:
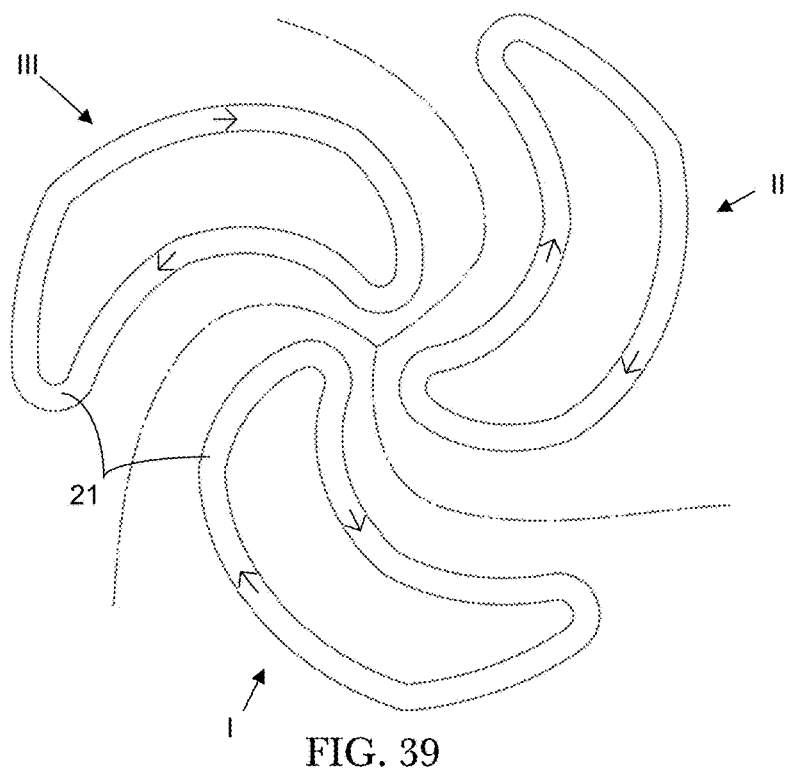
FIG. 39 is a top view of a three-flutter-coil configuration.
Figure 40:
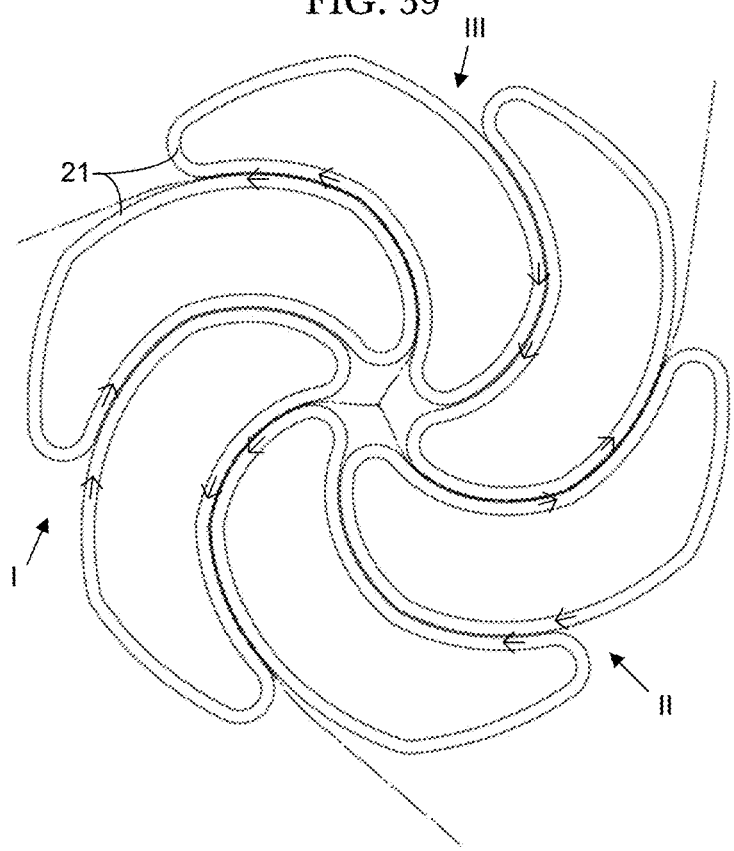
FIG. 40 is a top view of a six-flutter-coil configuration.

As shown in the embodiments of FIGS. 19, 28, 29 and 35, six (or three) flutter coils 21 can be provided in a three-sector configuration in the isochronous cyclotron 85. A design with three evenly spaced flutter coils 21 is shown in FIG. 39, while a design with six flutter coils 21 is shown in FIG. 40. FIGS. 28 and 29 show two sets of flutter coils 21' and 21" in a six-coil configuration. If the electric current flows through the coils 21' in the first set in a clockwise direction, the electric current flows through the coils 1" is the second set in a counter-clockwise direction. Each flutter coil 21 can have a cross section of 15×80 mm and can be formed of 640 turns (windings) of the superconductor wire with a current density of $J_{e/WP}$ of 263 A/mm$^2$). Each flutter coil can operate at a maximum temperature, $T_{max}$, of 4.80 K and can generate a maximum field, $B_{max}$, of 10.3 T. No known isochronous cyclotron of any existing configuration has a maximum field within a factor of two of this value of 10.3 T.

Figure 19:
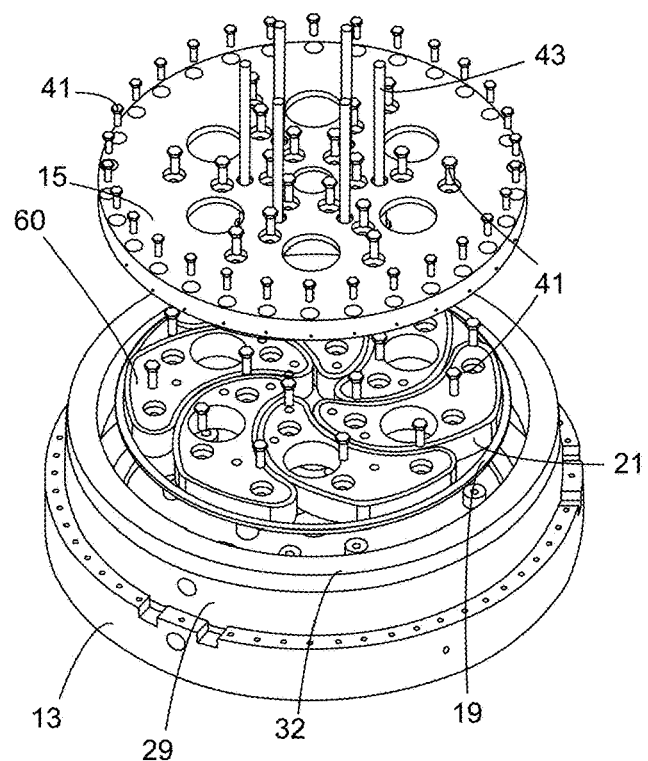
FIG. 19 includes a perspective view and an exploded view of components in a cold mass (including six flutter coils 21) in an embodiment of the isochronous cyclotron.

FIG. 19 is an exploded view of components in a cold mass of an embodiment of the isochronous cyclotron 85. This embodiment includes six flutter coils 21 (formed of $Nb_3Sn$) about an internal reinforcement structure 60 (formed of AISI3016 stainless steel) and under a base plate cover 15 (formed of AI6061-T6 aluminum alloy) secured via bolts 41 the rest of base plate 13 (also formed of AI6061-T6 aluminum alloy). Center support links 43 pass through the base plate cover 15. Also shown is a superconducting primary coil 32, and a copper wrap 29 around the primary coil 32. The auxiliary coil 19, shown in FIG. 19 modifies the edge radial magnetic field to reach full energy.

Figure 30:
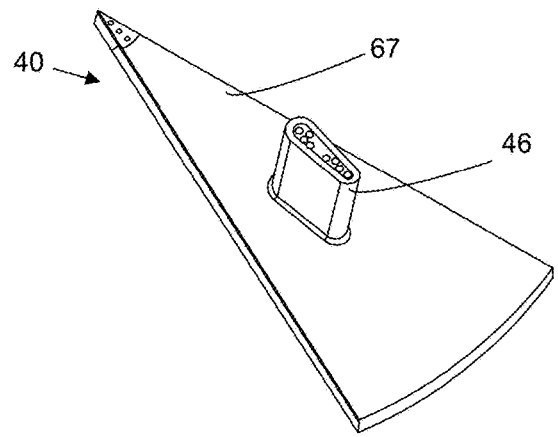
FIG. 30 shows one of six radiofrequency (RF) electrode dees for use in an embodiment of the isochronous cyclotron.
Figure 31:
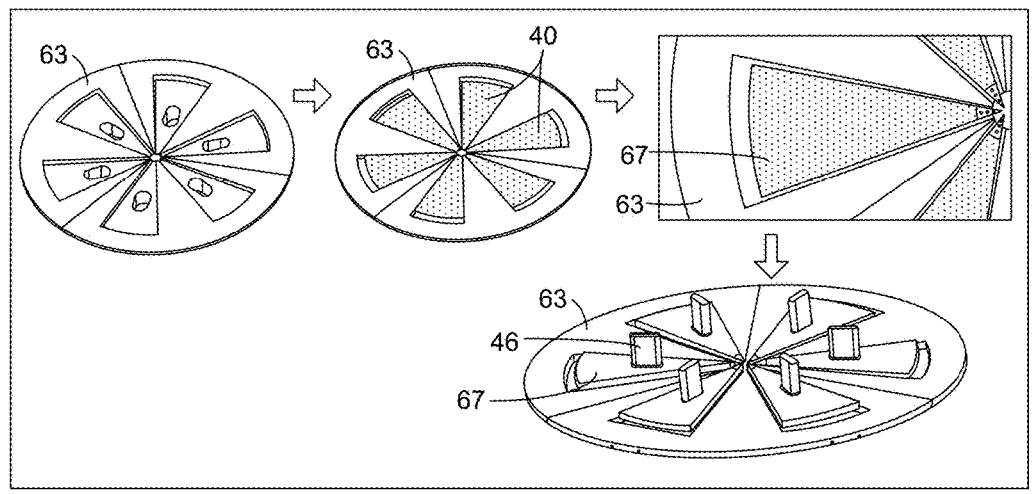
FIG. 31 shows a fabrication and assembly process for an embodiment of the dee assembly for use in the isochronous cyclotron.
Figure 32:
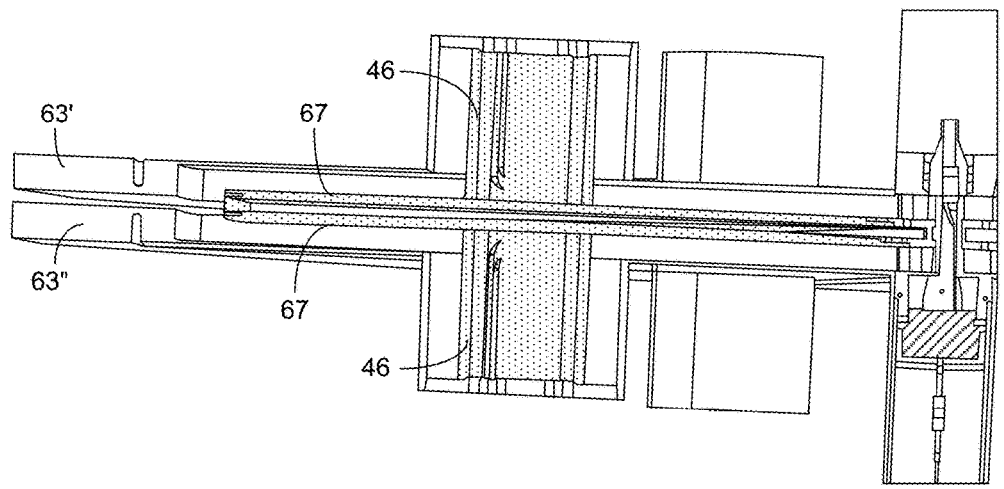
FIG. 32 show additional sectional views of the fabrication and assembly of an embodiment of the isochronous cyclotron.

An embodiment of one of six radiofrequency (RF) electrode dees 40 for the six-flutter-coil configuration is shown in FIG. 30. The dee 40 includes an electrode plate 67 and a stem 46. A top/bottom plate 63 for mounting the six dees 40 is shown in FIG. 31, wherein the stems 46 of the dees 40 are brazed into respective slots in the plate 63. As shown in the last image of FIG. 31 and in FIG. 32, the electrode plates 67 of respective electrode dees 40 are stacked across from each other, one brazed in a top plate 63' and the other brazed in a bottom plate 63", with the median acceleration plane 26 extending between each pair of electrode plates 67.

Figure 33:
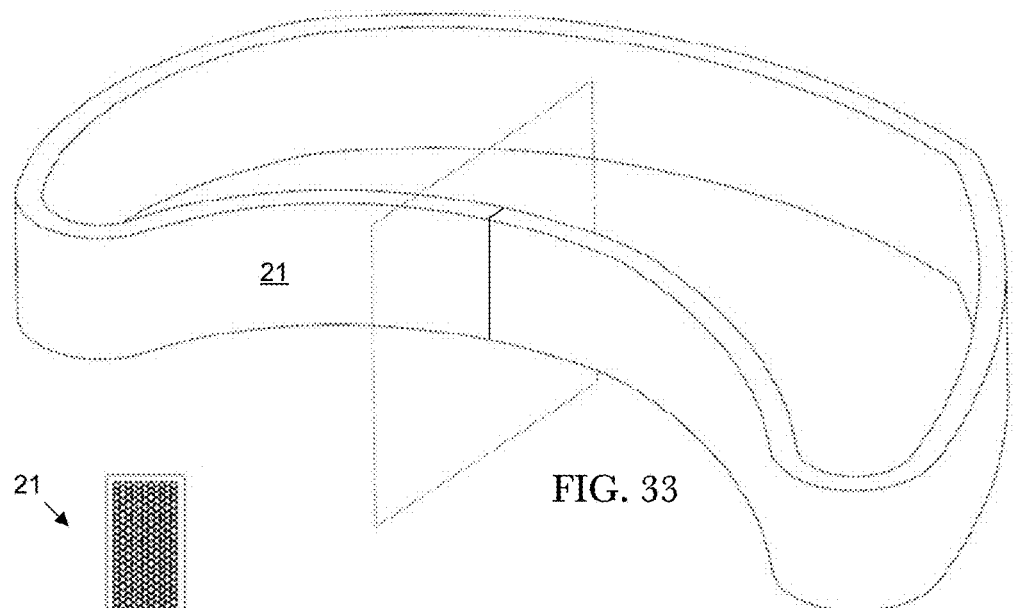
FIG. 33 shows a flutter coil 21 used in an embodiment of the isochronous cyclotron.
Figure 34:
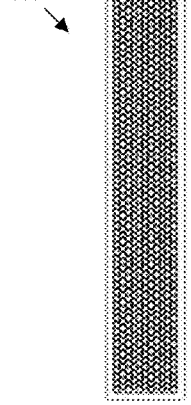
FIG. 34 shows a sectional view of the flutter coil 21 of FIG. 34, showing the round cross-sections in the wire windings that form the flutter coil 21.
Figure 35:
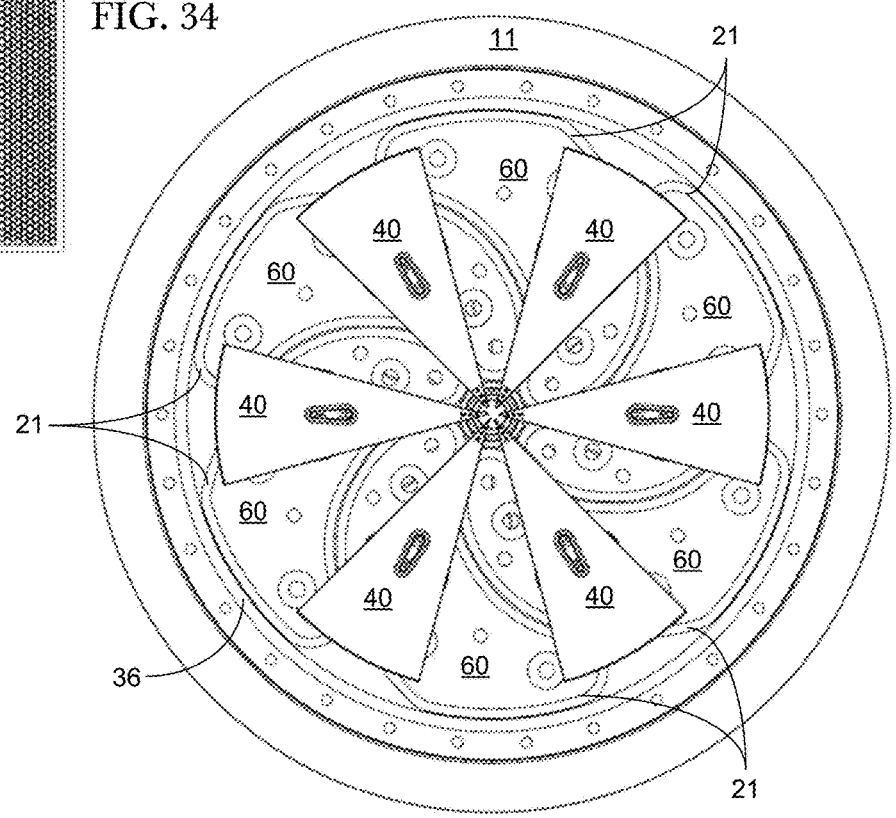
FIG. 35 shows an overlay of the RF dee electrodes over the flutter coils 21 in an embodiment of the isochronous cyclotron

The flutter coils 21 can be formed of a single-strand low-temperature superconductor wire (e.g., NbTi, Nb$_3$Sn, Nb$_3$Al with a round cross-section having a diameter of, e.g., 0.5 mm to 2.0 mm). The wire is initially formed of reactant (e.g., niobium and tin) powders and is outwardly wound many times (e.g., over 100 individual turns, as shown in FIG. 34) around a mandrel. Then, after winding, the powders are reacted (e.g., for 200 hours at 600 K) to produce the superconductor (e.g., Nb$_3$Sn). The reacted wire windings are then permeated with a fiber-glass/epoxy matrix that sets the overall shape and provides mechanical support from thermal contraction and magnetic stresses in the resulting flutter coil, as seen in FIG. 33. The composite flutter coils 21 are then covered with a ground wrap formed, e.g., of epoxy-glass composite. The flutter coils 21 are designed to have a low inductance (lower than that of the primary coils 30 and 32). The composite flutter coil 21 can have a cross-sectional height of less than 20 cm and a width of less than 10 cm. Although the flutter coils 21 and RF electrodes are both shown in FIG. 35, they are separated by the cryostats 56 in the assembled isochronous cyclotron 85—the flutter coils 21 are contained in the upper and lower cryostats 56, while the RF electrodes are positioned between the cryostats 56. In other embodiments, the RF electrodes can have a spiral shape.

Figure 12:
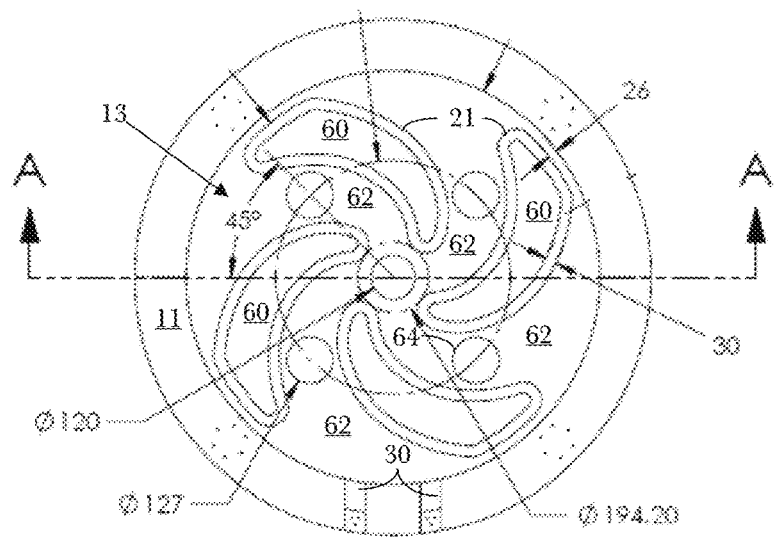
FIG. 12 is a top view of the base plate 13 with the superconducting coils 21 and 30 and bobbin 11, showing the section (A-A) from which the view of FIG. 11 was taken.

The non-magnetic external reinforcement support structure 62, as shown in FIG. 12, can be formed of a metal, such as aluminum, and the internal reinforcement structure 60 can be formed of a metal, such as stainless steel or copper; and these compositions can provide the respective rates of contraction with decreasing temperature to produce flush contact between these structures at the cryogenic operating temperature. In particular embodiments, the coefficient of thermal expansion (CTE) of the composition of the internal reinforcement structure 60 is less than the CTE of the composition of the flutter coil 21; and the CTE of the composition of the flutter coil 21 is less than the CTE of the non-magnetic external reinforcement structure 62. In other words, the flutter coils 21 contract more than the internal reinforcement structure 60; and the external reinforcement structure 62 contracts more than the flutter coils 21 to put the entire structure under compression with cooling. The compositions of the external reinforcement structure 62 and the internal reinforcement structure 60 can also be non-magnetic and have high thermal conductivities.

Figure 20:
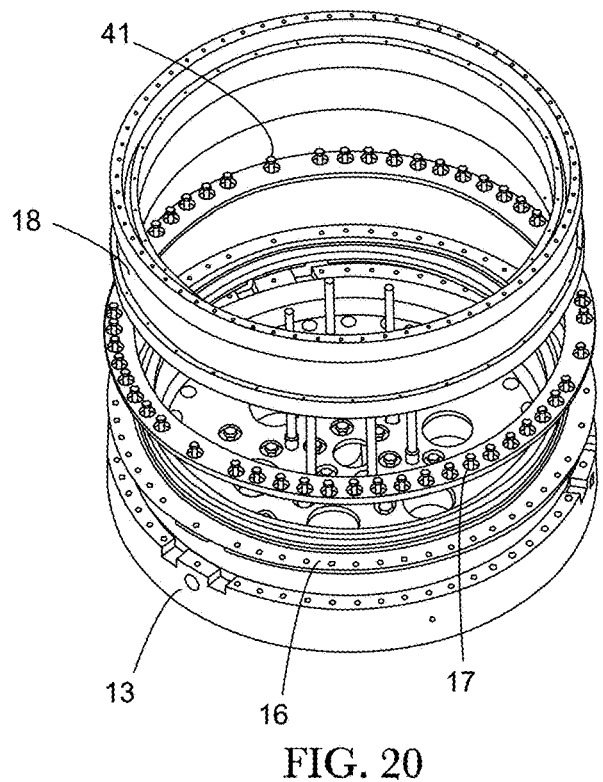
FIG. 20 includes a perspective view and an exploded view of components in the cold mass of FIG. 19 with axial support.
Figure 21:
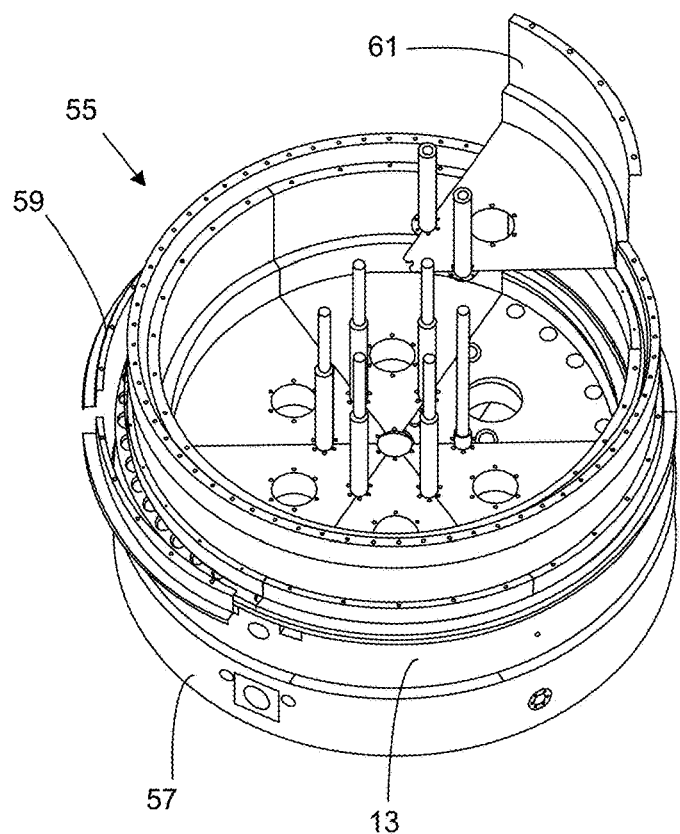
FIG. 21 includes a perspective view and a partially exploded view of a cryostat heat shield 55 in an embodiment of the isochronous cyclotron.
Figure 22:
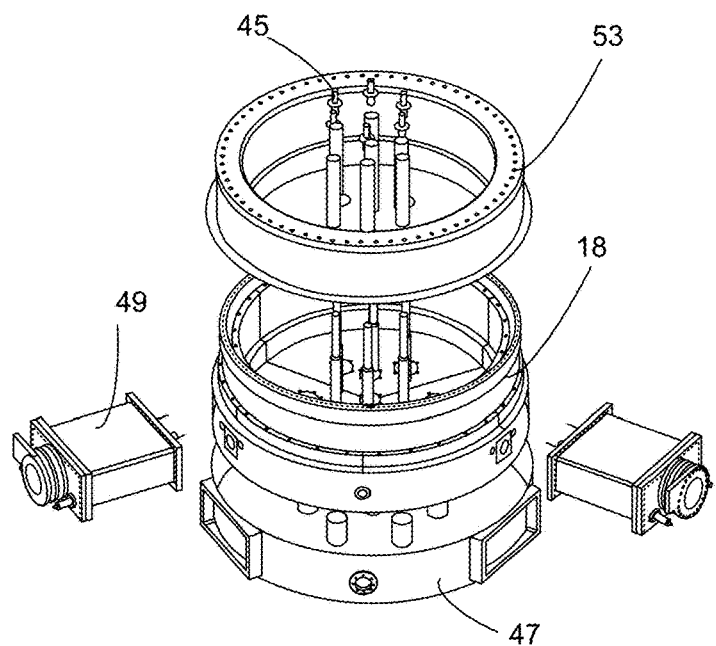
FIG. 22 includes a perspective view and an exploded view of a cryostat assembly in an embodiment of the isochronous cyclotron.

An exploded view of support components for the cold mass of FIG. 19 is shown in FIG. 20, including a cover 16 for primary coil 32, a cover mount 17, and axial support ring 18. Both the cover 16 and the cover mount 17 can be formed of an austenite nickel-chromium-based superalloy (e.g., Inconel 718 alloy). A perspective (and partially exploded) view of a cryostat heat shield 55 is shown in FIG. 21, including a heat shield base 57, a mount 59 for the base 57 and heat-shield center segments 61, all of which can be formed of copper alloy (e.g., CU10100). Furthermore, a perspective and exploded view of cryostat assembly is shown in FIG. 22, including cryocooler boxes 49 (through which the cryocoolers 38 pass) coupled with the cryostat vacuum chamber base 47, along with center support mounts 45 [formed of an austenite nickel-chromium-based superalloy (e.g., Inconel 718 alloy)] and cryostat vacuum cover 53. The cryocooler boxes 49 can also be formed of an austenite nickel-chromium-based superalloy (e.g., Inconel 718 alloy), while the cryostat vacuum cover 53 and cryostat vacuum chamber base 47 can be formed of 316 stainless steel.

Figure 23:
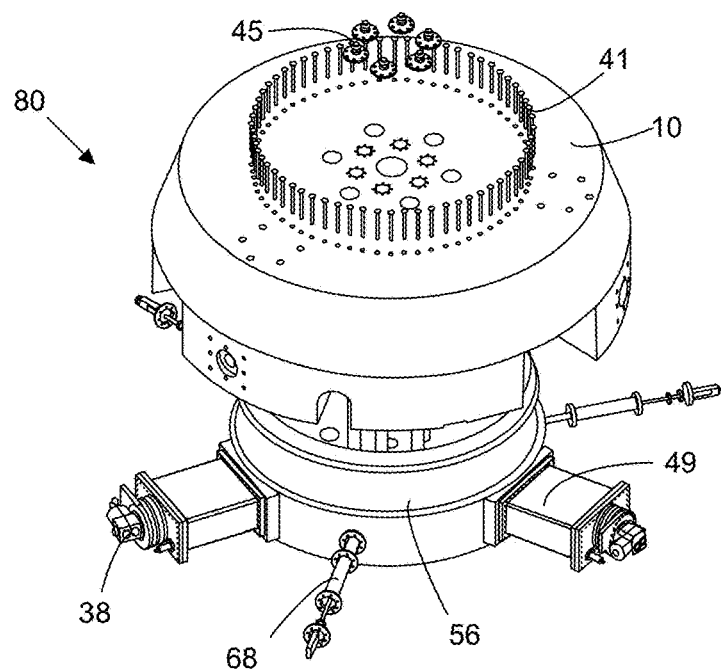
FIG. 23 includes a perspective view and an exploded view of the upper half 80 of an embodiment of the isochronous cyclotron.
Figure 24:
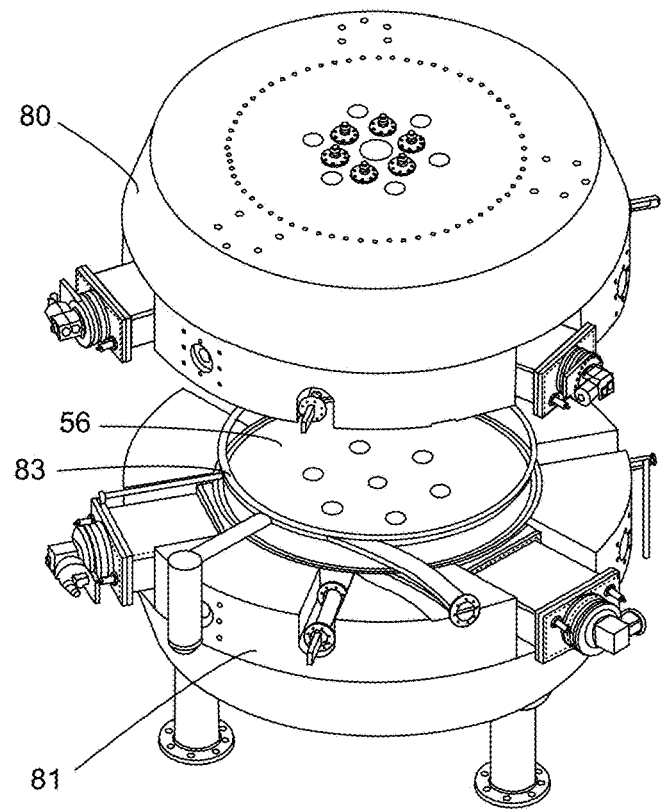
FIG. 24 includes a perspective view of an embodiment of the isochronous cyclotron and an exploded view showing the separated upper and lower halves 80 and 81 of this isochronous cyclotron.
Figure 25:
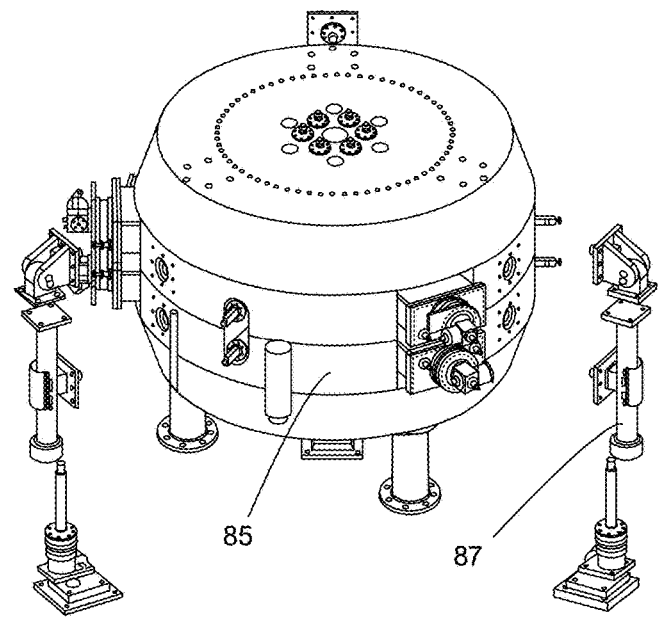
FIG. 25 shows the top and bottom halves of the cyclotron with a jacking system 87.

A perspective and exploded view of an upper half 80 of a cyclotron 85 is shown in FIG. 23, with a yoke 10 formed of iron (e.g., 1010 steel) surrounding the cryostat 56 from which the radial support links 68 (formed, e.g., of 316 stainless steel) and cryocoolers 38 extend. The upper 80 and lower 81 halves of the cyclotron, each containing a respective cryostat 56, are shown in the exploded perspective view of FIG. 25, with a vacuum ring 83 positioned there between. FIG. 25 shows the jacking system 87 coupled with the cyclotron 85.

Figure 26:
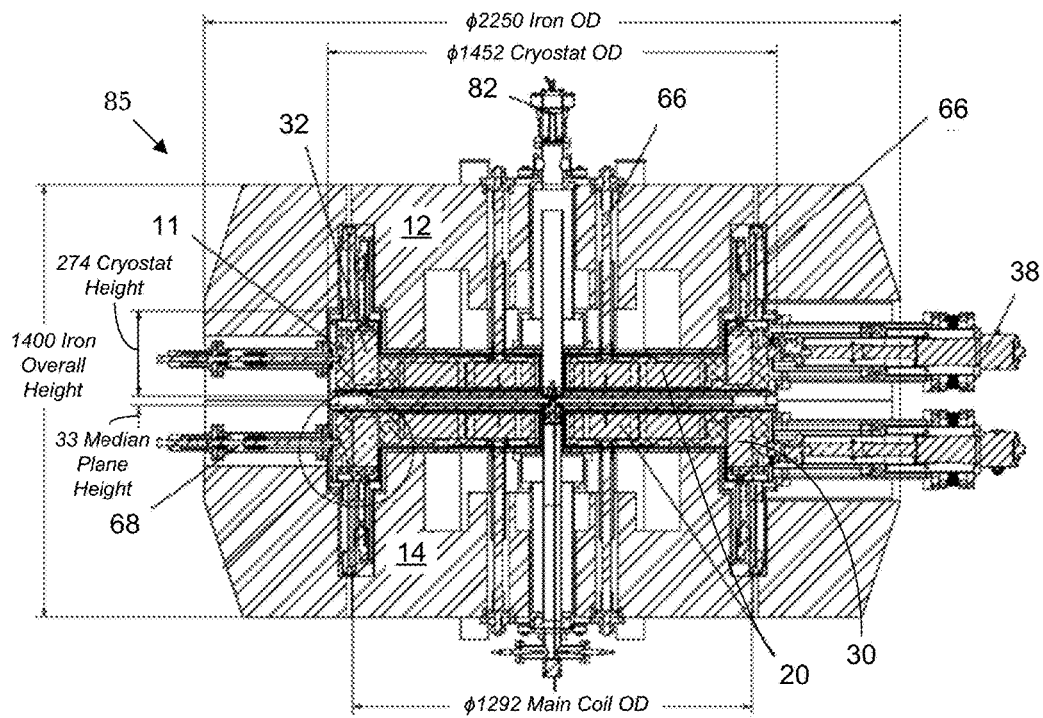
FIG. 26 shows a cross-section of an embodiment of the isochronous cyclotron.
Figure 27:
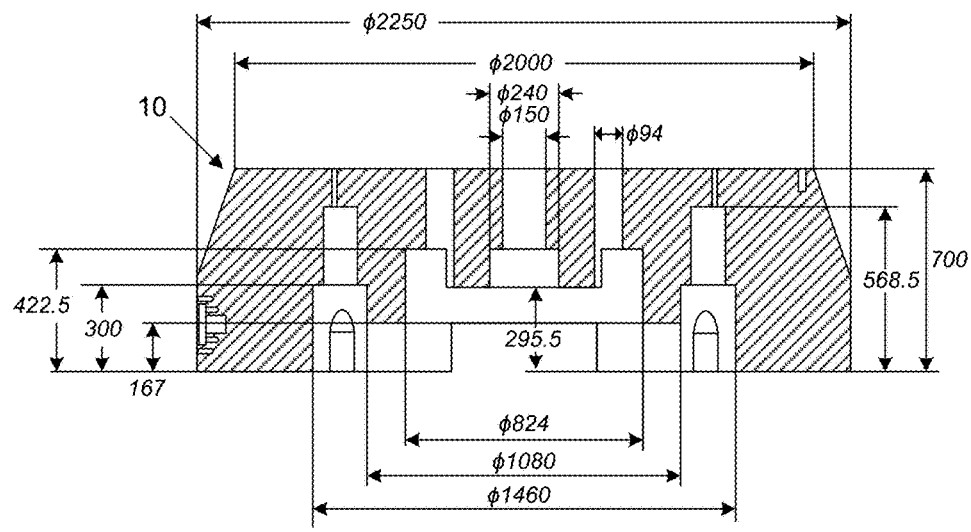
FIG. 27 shows a sectional view of the magnet iron yoke 10 in an embodiment of the isochronous cyclotron.

Another sectional view of an embodiment of the isochronous cyclotron 85 is provided in FIG. 26, showing the ion source 82, axial supports 66, radial supports 68, cryocoolers 38, flutter-coil assemblies 20, primary coils 30 and 32, and bobbins 11. A sectioned view of the top half of a yoke 10 for the cyclotron 85 is provided in FIG. 27. The yoke 10 can be formed of AISI 1010 steel with an elastic modulus of 190 GPa and a yield strength of 305 MPa, and the entire yoke 10 can weigh about 14 tons (12,700 kg).

Figure 3:
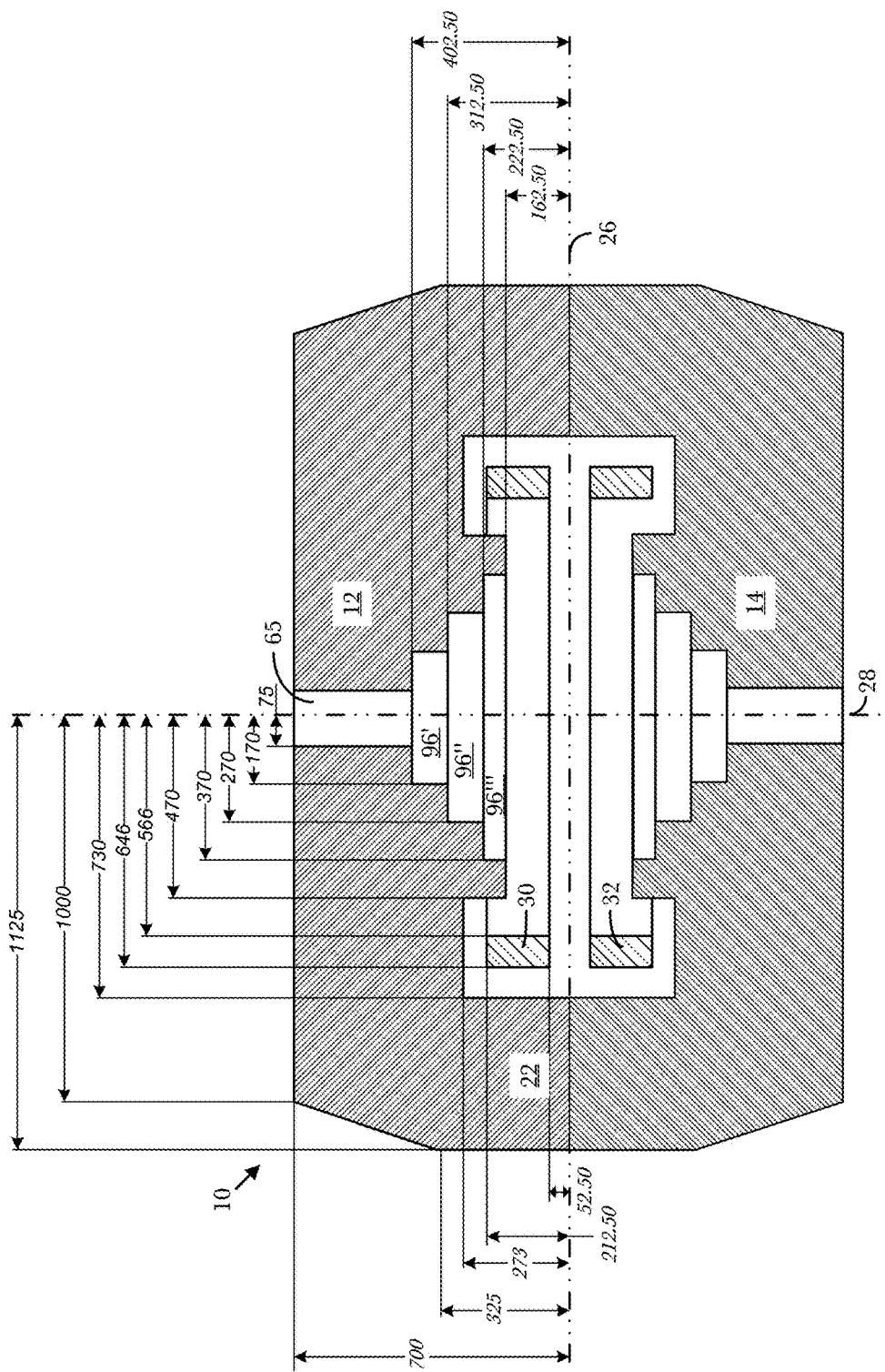
FIG. 3 is a sectional side view of the yoke 10 and primary coils 30 and 32 in the isochronous cyclotron of FIG. 1, where the indicated measurements are in millimeters.
Figure 5:
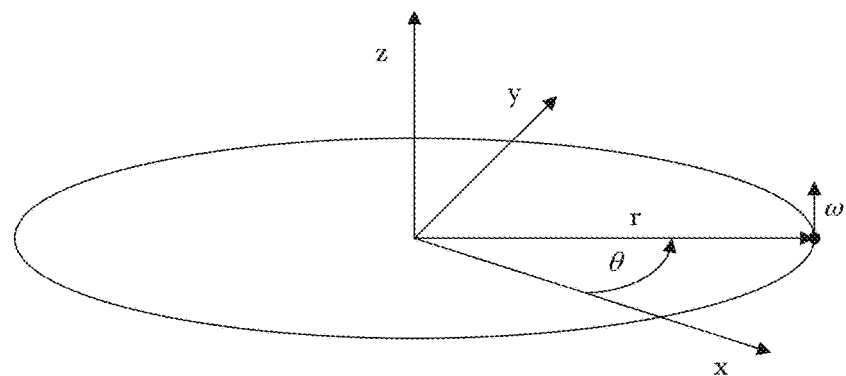
FIG. 5 is a sketch of the axial reference frame for the ion orbits inside the isochronous cyclotron.

The yoke 10 of the isochronous cyclotron 85 can be designed to produce a 100-300-MeV beam, as shown in FIG. 1, can have a diameter of 2 meters across its base and top surfaces (in the orientation shown) and a height of about 1.4 m (measured vertically along the z-axis in the illustrated orientations in accord with the coordinate framework provided in FIG. 5). A central cylindrical channel 65 with a diameter of 150 mm for ion injection is defined by the poles 12 and 14. The top-most cylindrical cutout section 96' has a height of 90 mm and a diameter of 340 mm and extends to a distance of 297.5 mm of the top surface. The middle cylindrical cutout section 96" has a height similar to that of the top-most cutout section 96' and a diameter of 540 mm. The bottom cylindrical cutout section has a height of 60 mm and a diameter of 740 mm. The beam chamber 24 has a height of 37 mm. The various dimensions (in mm) of the yoke 10 and other components of the cyclotron 85 are also indicated in FIG. 3. The base plate 13 (as shown in FIG. 8) can be 36.5 mm from the median acceleration plane 26, and a 0.6-mm-thick wall of the non-magnetic composition of the external reinforcement structure 62 extends between (a) the flutter coils 21 (within which the internal reinforcement structure 60 is contained) and (b) the inner wall (facing the beam chamber 24) of the base-plate section 90 of the cryostat 56. The superconducting primary coils 30 and 32 can be separated by a distance of about 114 mm on opposite sides of the median acceleration plane 26.

Together, the superconducting primary coils 30 and 32 and the yoke 10 [including the return yoke 22, poles 12 and 14, and spiral flutter coils 21] generate a peak combined field, e.g., of 4-6 Tesla in the median acceleration plane 26 (with the magnetic field increasing at greater radii). The superconducting primary coils 30 and 32 can directly generate a magnetic field in the median acceleration plane 26, e.g., of 3.6 Tesla or greater, when a voltage is applied thereto to initiate and maintain a continuous superconducting current flow through the superconducting primary coils 30 and 32. The yoke 10 is magnetized by the field generated by the superconducting primary coils 30 and 32 and contributes to the magnetic field generated in the chamber 14 for ion acceleration.

Both of the magnetic field components (i.e., both the field component generated directly from superconducting primary coils 30 and 32 and the field component generated by the magnetized yoke 10) pass through the median acceleration plane 26 approximately orthogonal to the median acceleration plane 26. The yoke 10 is configured (including the pole cut-outs 96 where the gap between the poles 12 and 14 is increased) to shape the magnetic field along the median acceleration plane 26 so that the magnetic field increases with increasing radius from the central axis 28 to the radius at which ions are extracted in the beam chamber 24 to compensate for relativistic particle mass gain during acceleration.

The voltage to maintain ion acceleration is provided at all times via current lead to pairs of high-voltage electrode dees 40 that are oriented parallel to and above and below the median acceleration plane 26 inside the beam chamber 24. The yoke 10 is configured to provide adequate space for the electrode dees 40, which extend through a vacuum feed-through in the magnet structure. The electrode apparatus is formed of a conductive metal, the number of electrode dees 40 can match the number of flutter coils 21, with each electrode dee 40 positioned at angles between adjacent flutter coils 21 (but closer to the median acceleration plane 26 than the flutter coils 21) in a ring about the central axis 28.

The electrode dees 40 are fed with an RF voltage (e.g., at 205.7 MHz for third-harmonic solutions) by RF current leads, which are fed parallel to the vertical (z) axis through the RF-lead apertures 64 through the non-magnetic external reinforcement structure 62, to excite the dees 40 to have an oscillating voltage at the cyclotron frequency or at an integer multiple of the cyclotron frequency. The frequency of the voltage delivered to each coil 21 can be four times the orbital frequency of the accelerating ion (e.g., a voltage frequency of 272 MHz where the ion orbits in the beam chamber 24 at a frequency of 68 MHz); and the RF voltage delivered to the respective flutter coils 21 can be sequenced so that the accelerating ion is subject to peak voltages when aligned with each of the coil edges with 180 degree spans in the voltage sine wave across each dee 40 and between each dee 40.

During operation, the superconducting primary coils 30 and 32 can be maintained in a "dry" condition (i.e., not immersed in liquid refrigerant); rather, superconducting primary coils 30 and 32 can be cooled to a temperature below the superconductor's critical temperature (e.g., as much as 5K below the critical temperature, or in some cases, less than 1K below the critical temperature) by one or more cryogenic refrigerators (cryocoolers) 38. In other embodiments, the superconducting primary coils 30 and 32 can be in contact with a liquid cryogen for heat transfer from the superconducting primary coils 30 and 32 to the cryogenic refrigerator 38. When the superconducting primary coils 30 and 32 are cooled to cryogenic temperatures (e.g., in a range from 4K to 30K, depending on the composition), the base plate 13 is likewise cooled to approximately the same temperature due to the thermal contact among the cryocooler 38, the bobbin 11, superconducting primary coils 30 and 32, the non-magnetic external reinforcement structure 62, the flutter coils 21, and the internal reinforcement structure 60.

Figure 2:
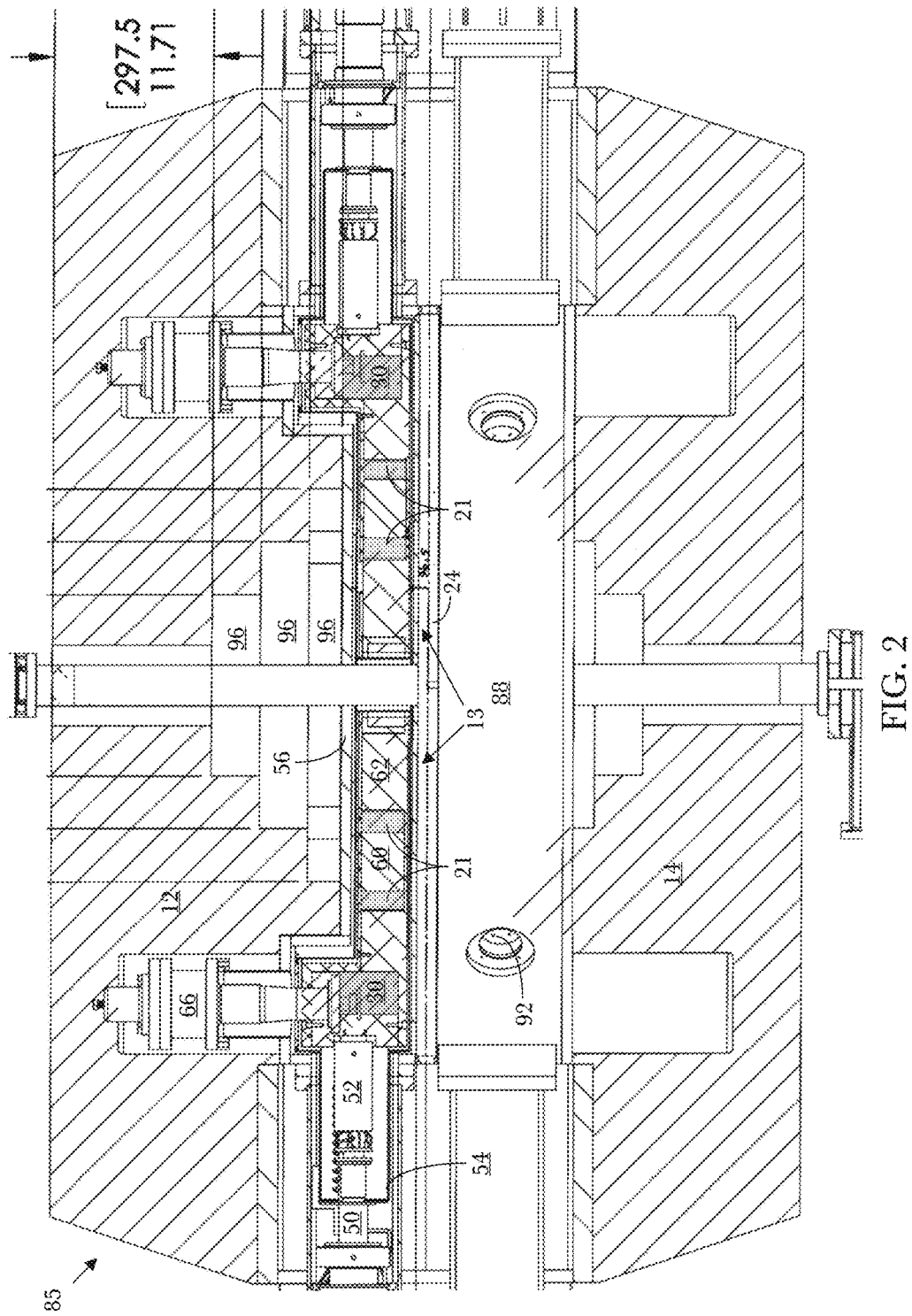
FIG. 2 is a magnified view of a cryostat 56, a base plate 13 and the beam chamber 24 from the isochronous cyclotron of FIG. 1.

The cryocooler 38 can utilize compressed helium in a Gifford-McMahon refrigeration cycle or can be of a pulse-tube cryocooler design with a higher-temperature first stage 50 and a lower-temperature second stage 52 (shown in FIGS. 1 and 2). The lower-temperature second stages 52 of the cryocoolers 38 can be operated at about 4.5 K and thermally and mechanically (e.g., via bolts) coupled with the bobbin 11, which is in close thermal contact with the superconducting primary coils 30 and 32 and the base plate 13. The cryocooler 38 can accordingly cool each superconducting primary coil 30/32 and each superconducting flutter coil 21 to a temperature (e.g., about 4.5 K) at which the conductor in each coil 30/32/21 is superconducting. Alternatively, where a higher-temperature superconductor is used, the second stage 52 of the cryocooler 38 can be operated at, e.g., 4-30 K.

The warmer first stage 50 of the cryocooler 38 can be operated at a temperature of, e.g., 40-80 K and can be thermally coupled with the intermediate thermal shield 54 that is accordingly cooled to, e.g., about 40-80 K to provide an intermediate-temperature barrier between the magnet structure (including the yoke 10 and other components contained therein) and the cryostats 56 (shown in FIG. 8), which can be at room temperature (e.g., at about 300 K). The cryostats 56 include a vacuum port 58 to which a vacuum pump can be coupled to provide a high vacuum inside the cryostats 56 and thereby limit convection heat transfer between the cryostats 56, the intermediate thermal shield 54 and the magnet structure 10. The cryostats 56, thermal shield 54 and the yoke 10 can each be spaced apart from each other by an amount that minimizes conductive heat transfer; and these structures can be structurally supported by insulating spacers.

The magnetic yoke 10 provides a magnetic circuit that carries the magnetic flux generated by the superconducting primary coils 30 and 32 to the beam chamber 24. The magnetic circuit through the magnetic yoke 10 (in particular, the azimuthally varying field provided by the flutter coils 21) also provides field shaping for strong focusing of ions in the beam chamber 24. The magnetic circuit also enhances the magnetic field levels in the portion of the beam chamber 24 through which the ions accelerate by containing most of the magnetic flux in the outer part of the magnetic circuit. In a particular embodiment, the magnetic yoke 10 (except the flutter coils 21) is formed of low-carbon steel, and it surrounds the superconducting primary coils 30 and 32. Pure iron may be too weak and may possess an elastic modulus that is too low; consequently, the iron can be doped with a sufficient quantity of carbon and other elements to provide adequate strength or to render it more stiff while retaining the desired magnetic levels.

Figure 9:
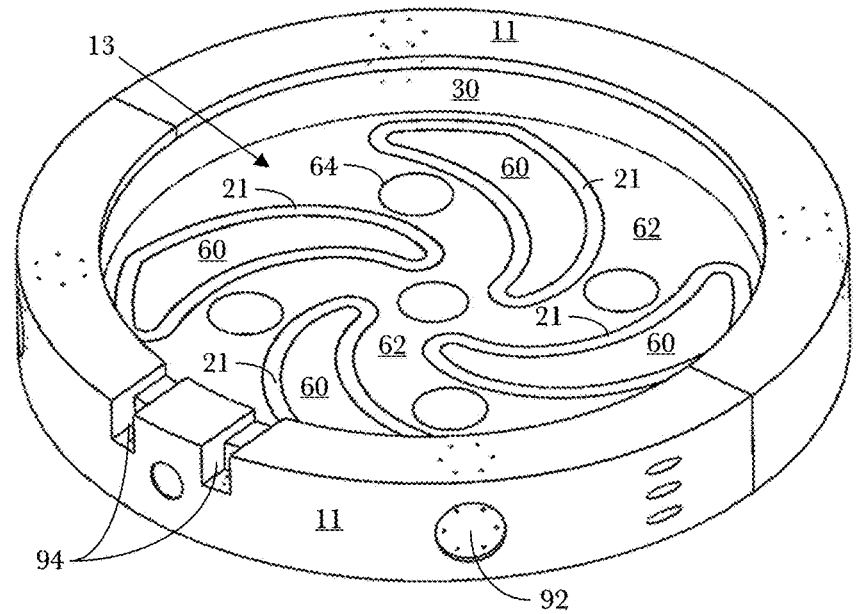
FIG. 9 is a perspective view of a base plate assembly, which is contained inside a cryostat, wherein the base plate assembly includes a base plate 13, a primary coil 30 and a bobbin 11.
Figure 10:
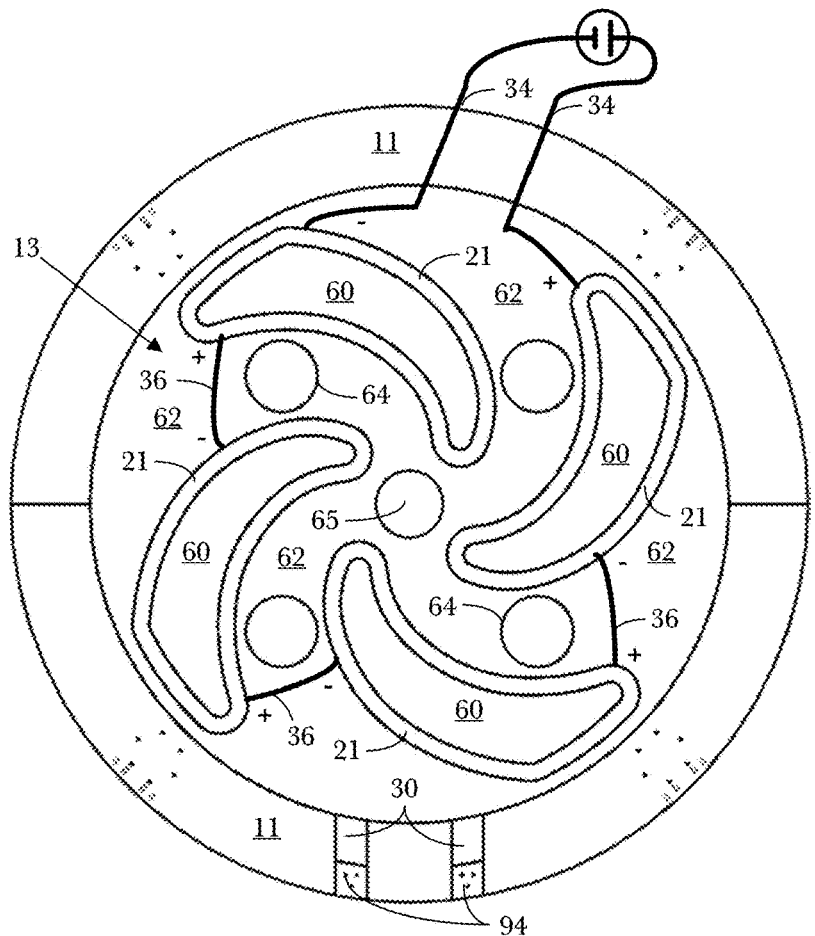
FIG. 10 is a top view of the base plate assembly shown in FIG. 9.
Figure 11:
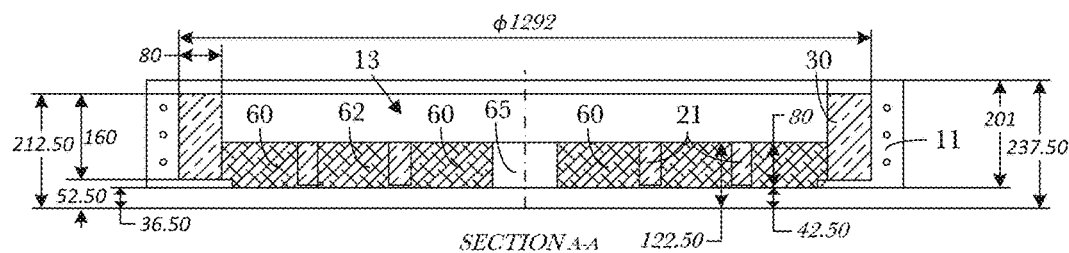
FIG. 11 is a sectional side view of the base plate 13 with the superconducting primary and flutter coils 30 and 21 and bobbin 11, where the indicated measurements are in mm.

The embodiment illustrated in FIGS. 9 and 10 includes four spiral superconducting flutter coils 21 on each side of the median acceleration plane 26, though other embodiments can include, for example, three, six or eight evenly spaced flutter coils 21 on each side of the median acceleration plane 26. Three and six flutter-coil configurations are shown, respectively in FIGS. 39 and 40, wherein the number of sectors, N, is three for each of the three- and six-coil configurations. The flutter coil sectors I, II, and III are illustrated in FIGS. 39 and 40, and the direction of current flow through each flutter coil 21 is shown with arrows (FIG. 39 shows the current flow, $I_2$, in each flutter coil 21 as being in a clockwise direction, though the current, $I_2$, can alternatively be in a counter-clockwise direction in each flutter coil 21. As shown, the flutter coils 21 in the three-coil configuration can be fatter (including more amp-turns per coil 21) than the four-coil configuration. Accordingly, the current, $I_2$, in the three-coil configuration is stronger than the current, $I_1$, in the six-coil configuration. For example, $I_2$ can approximately equal $2 \times I_1$, and the same is true for four- and eight-coil configurations.

Three or six coil configurations of flutter coils 21 are considered to be N=3 sector Isochronous cyclotrons with three identical 120 degree angular width magnetic sectors per pole face. In three-coil embodiments, the flutter coil current direction is the same in all three coils 21. In the six-flutter-coil embodiments, the flutter coil current direction alternates clockwise and counterclockwise from one coil 21 to the next coil 21 (sequentially) when viewed from above. Four- or eight-coil configurations of flutter coils 21 are considered to be N=4 sector Isochronous cyclotrons with four identical 90 degree angular width magnetic sectors per pole face. In four-coil embodiments, the flutter coil current direction is the same in all four coils 21. In the eight-coil embodiments, the flutter coil current direction alternates clockwise and counterclockwise from one coil 21 to the next coil 21 (sequentially) when viewed from above.

A radial orbit stability argument [see John J. Livingood, "Principles of Cyclic Particle Accelerators", D. Van Nostrand Co., Princeton, N.J., p 239-240 (1961)] suggests that for protons beams of final energy in excess of 200 MeV, the minimum sector number must be N=4 sector, and that N=3 sector proton cyclotrons with final energies above 200 MeV are forbidden. Specifically, this radial stability argument posits that the radial orbit oscillations in an isochronous cyclotron are stable if $v_r$<N/2. For N=3 sector cyclotrons, $v_r$<1.5 shall be true. Since $v_r$~$\gamma$ in isochronous cyclotrons, the $\gamma$ being the relativistic factor for particle-mass gain with acceleration, this would limit the final $\gamma$<1.5, or a final energy of 0.5×proton rest mass–about 450 MeV. In practice, other factors add 0.3 to the final value of $v_r$, limiting $\gamma$<1.2, or a final energy of 200 MeV. With this invention, we have demonstrated, for the first time, that N=3 sector proton cyclotrons with final energies above 200 MeV are allowed. N=3 sector isochronous cyclotrons have more flutter and are inherently lower-cost and easier to construct because of the reduced flutter pole complexity.

The spiral-shaped flutter coils 21, as discussed above, serve as sector magnets to provide the azimuthal variation in the magnetic field, wherein the spiral shape enhances the variation in the field (i.e., the "flutter"). The superconducting flutter coils 21 can be formed of the same compositions as the primary coils 30 and 32 [e.g., a low-temperature superconductor, such as niobium titanium (NbTi), niobium tin ($Nb_3Sn$), or niobium aluminum ($Nb_3Al$); or a high-temperature superconductor, such as $Ba_2Sr_2Ca_1Cu_2O_8$, $Ba_2Sr_2Ca_2Cu_3O_{10}$, $MgB_2$ or $YBa_2Cu_3O_{7-x}$] and can have a round cross section and be wound, as discussed above. Where six or more flutter coils 21 are used, the RF voltage can be differentially applied to respective flutter coils 21 such that the electric current flows in each flutter coil 21 in a direction opposite to the direction in which the electric current flows in adjacent flutter coils 21.

A pair of base plates 13 with respective bobbins 11 and primary coils 30/32, as shown in FIGS. 9 and 10, are contained in the respective cryostats 56 (each with sections 88 and 90, as shown in FIG. 6). As shown in FIG. 8, section 88 of the cryostat 56 wraps around the base plate 13, which includes the flutter coils 21 and the surrounding non-magnetic external reinforcement structure 62. Cryocoolers 38 penetrate through the cryostats 56 from opposite sides to provide cryogenic cooling to the reinforced magnet structures contained therein.

Figure 41:
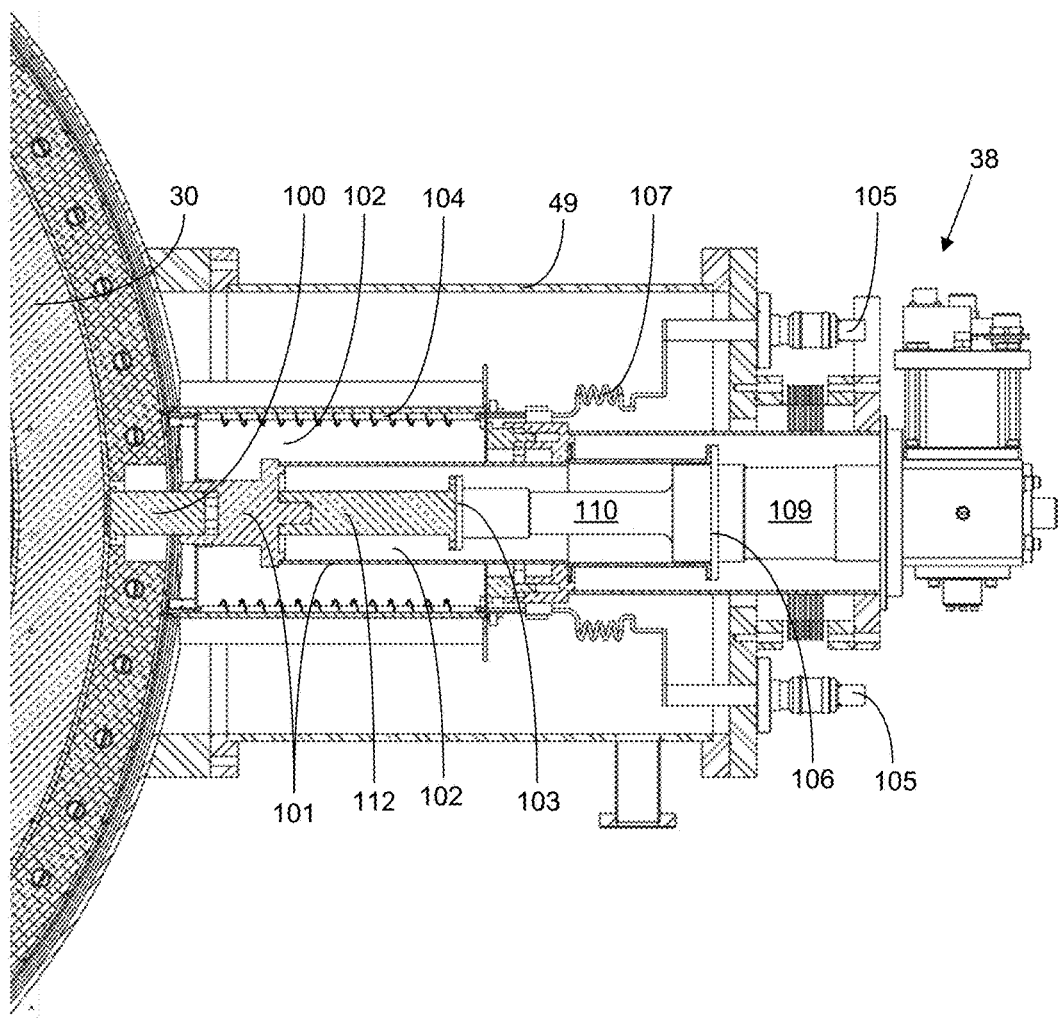
FIG. 41 is a top view of a horizontally mounted cryocooler 38.

The cryocoolers 38 are illustrated here and in FIG. 41 in a horizontal orientation. Each cryocooler 38 is joined, via a vacuum flange, to the cryocooler box 49 of the cryostat 56 As shown in FIG. 41, the cryocooler 38 also includes a cold foot anchor 100 (at 3-5 K) contacting (and in close thermal contact with) the primary superconducting coil 30/32. An integral maintenance boot assembly 101 is mounted on (and in close thermal contact with) the cold foot anchor 100 and extends to the first stage 109 of the cryocoler 38). The integral maintenance boot assembly 101 forms a link between the cold foot anchor 100 and the cold foot extension 112 leading to the second stage 110 of the cryocooler 38. The integral maintenance boot assembly 10 can be formed of a composite material with low thermal conductively, accordingly forming an insulating boot around the cold foot anchor 100 into which the cryocooler 38 can be replaceably inserted and removed (e.g., for maintenance or replacement) without breaking the vacuum in the cryostat and without having to warm up the magnet structure in the cyclotron 85. This configuration is in contrast with the traditional means for mounting a cryocooler, wherein the cryocooler is typically "hard connected" to a shield at the first stage and to the cold mass in the cyclotron at the second stage. The first-stage contact 106 of the cryocooler 38 (at the distal end of the first stage 109) can be maintained at 30-70 K, while the second-stage contact 103 of the cryocooler 38 (at the distal end of the second stage 110) can be maintained at 3-5 K. A vacuum is maintained in the volume 102 around the first and second stage of the cryocooler 38.

On each side of the cryopump 38 is a current-lead-and-vacuum feedthrough 105 through which electric current is supplied via an electrical bus (maintained in a near-vacuum environment) to the primary coil 30/32. The electrical bus includes a cold, resistive current lead 107 (formed, e.g., of copper) that feeds electrical current from a warm (room temperature) current lead to a high-temperature superconductor lead 104 (at 30-70 K where joined with the cold, resistive current lead 107). The high-temperature current lead 104, at its distal end, is in thermal contact with the primary superconducting coil 30/32 (at 3-5 K where joined with the high-temperature current lead 104. The surrounding cryostat, meanwhile is at room temperature (e.g., 293 K).

Figure 42:
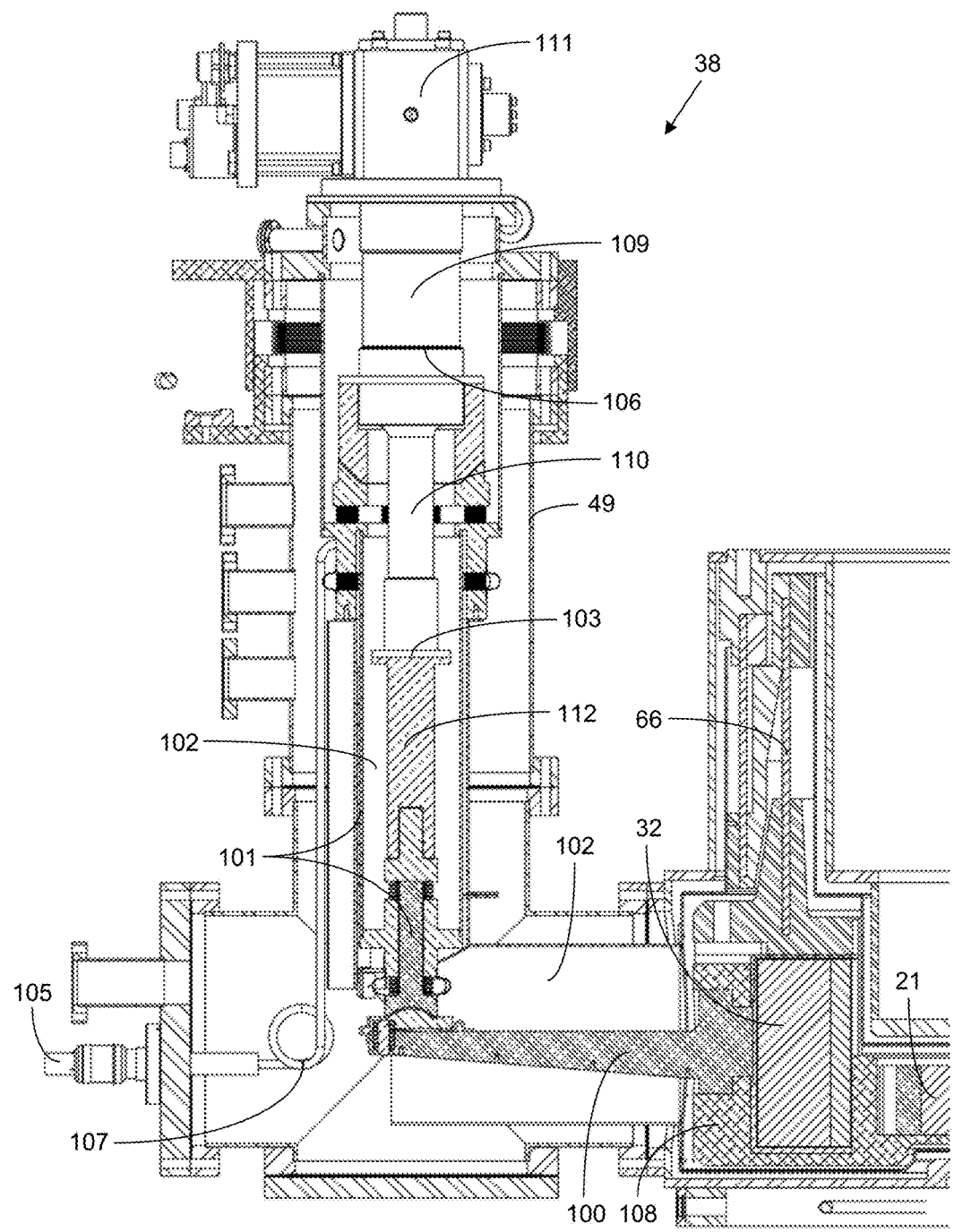
FIG. 42 is a side view of a vertically mounted cryocooler 38.

In an alternative embodiment, as shown in FIG. 42, the cryocoolers 38 can be folded vertically to reduce potentially damaging exposure to the magnetic field generated by the cyclotron 85. In this particular embodiment, the cold foot anchor 100 again extends horizontally (parallel to the median acceleration plane) from the primary coil 32 and cold mass 108. Here, however, the integral maintenance boot assembly is oriented orthogonally upward from the cold foot anchor 100 (and oriented orthogonally to the median acceleration plane). The first and second stages 109 and 110 of the cryocooler 38 are also oriented vertically, placing the head 111 of the cryocooler above the primary coil 32 and above the yoke of the cyclotron.

As seen in FIGS. 7 and 9-10, apertures 64 are also defined through the cryostats 56 and through the non-magnetic external reinforcement structure 62 to provide for passage of respective RF resonators there through to provide an RF voltage to each of the flutter coils 21 in the isochronous cyclotron 85. An additional aperture 65 through the cryostats 56 and non-magnetic external reinforcement structure 62 for ion injection or insertion of an ion injection device are shown.

Figure 4:
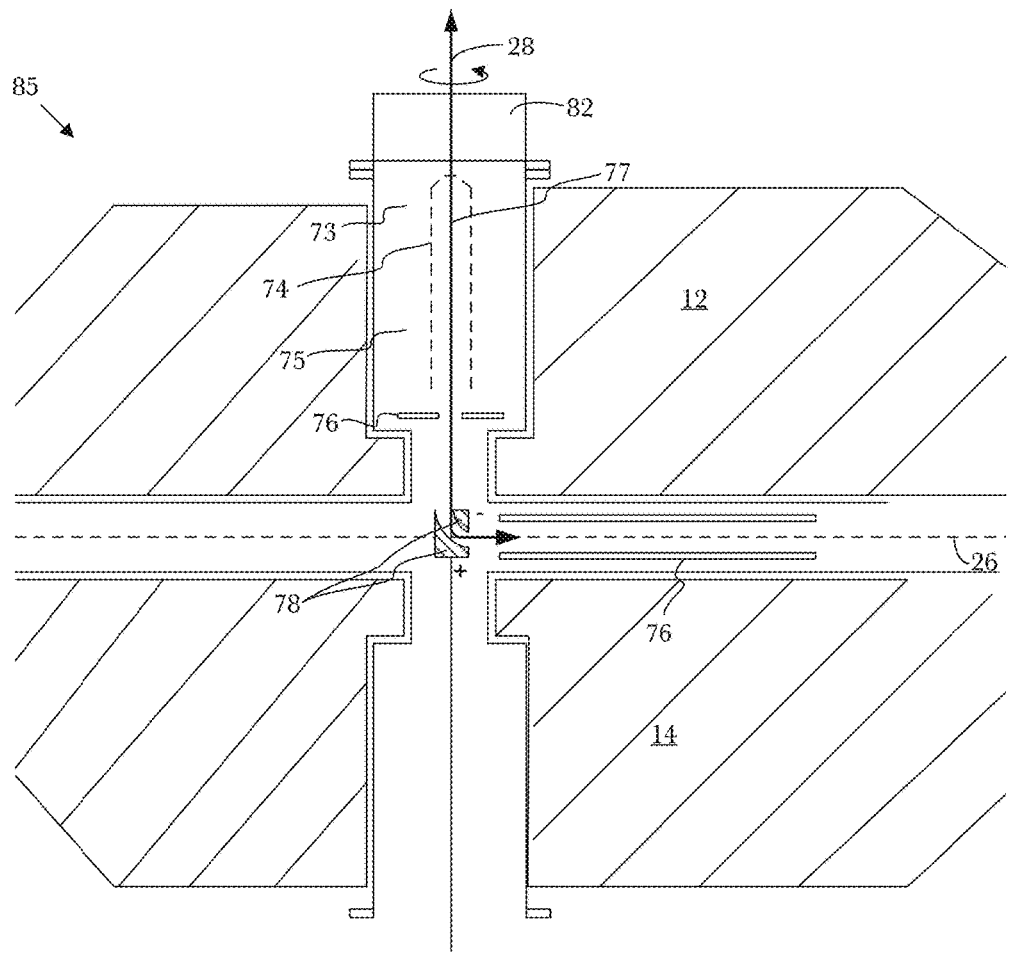
FIG. 4 is a sketch of a sectional side view of a high-intensity external ion injector mounted along the central axis 28 of an isochronous cyclotron.
Figure 37:
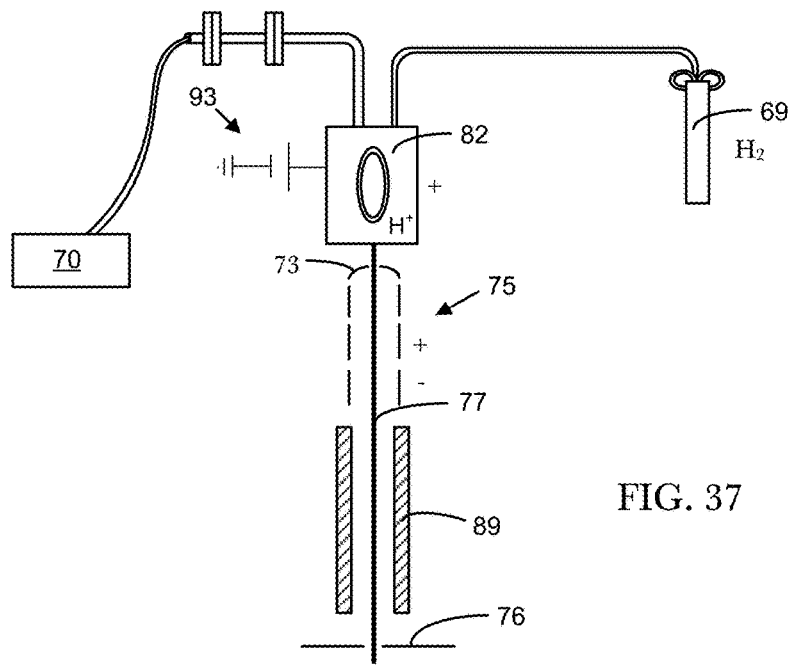
FIG. 37 is a sketch of an embodiment of the ECR ion source 82.

Embodiments of an external high-intensity ion injector 82 for injecting ions into the beam chamber 24 of the isochronous cyclotron 85 are shown in FIGS. 4 and 37, wherein an injector column 84 provides a pathway from an ECR ion source 82 in the ion injector 82 into the beam chamber 24. External to the cyclotron 85, a flow of a gas [e.g., hydrogen ($H_2$)] from a gas source 69 and microwaves from a microwave source 70 (at a frequency of 106 Hz) are directed into a plasma chamber 71 to form a plasma that emits a stream of ions 77 into the acceleration chamber of the cyclotron 85. Inside the plasma chamber, when protons are produced, electrons from a voltage source 93 collide with $H_2$ molecules from the hydrogen source 69 to produce (half the time) two hydrogen (H) ions and a free electron. When an electron collides with a hydrogen (H) ion, the product is $H^+$ and two electrons. In the other half of $H_2$/electron interactions, the collision of an electron with an H$_2$ molecule produces H$_2^+$ and two electrons. The H$^+$ ions (i.e., protons) can escape through an aperture 79 at the base of the plasma chamber 71.

Positive ions 77 (e.g., protons) passing through this aperture 79 into an injector column 84 where the protons first pass through an ion focus 73, fast deflection plates 74, a matching/stopping einzel lens triplet 75 and finally through a restriction aperture 76 before entering the beam chamber 24.

Figure 36:
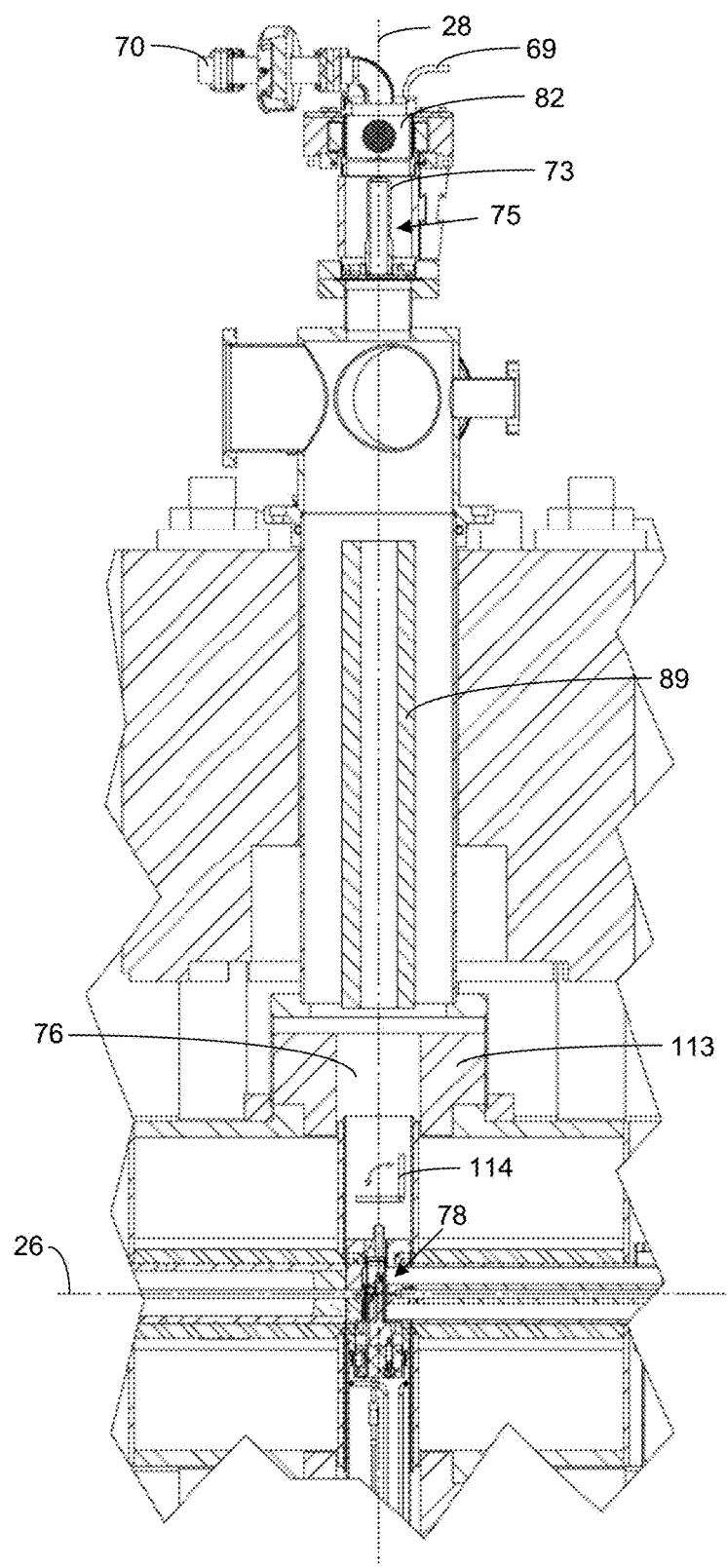
FIG. 36 shows a sectional view of an embodiment of the external ECR ion injector.
Figure 38:
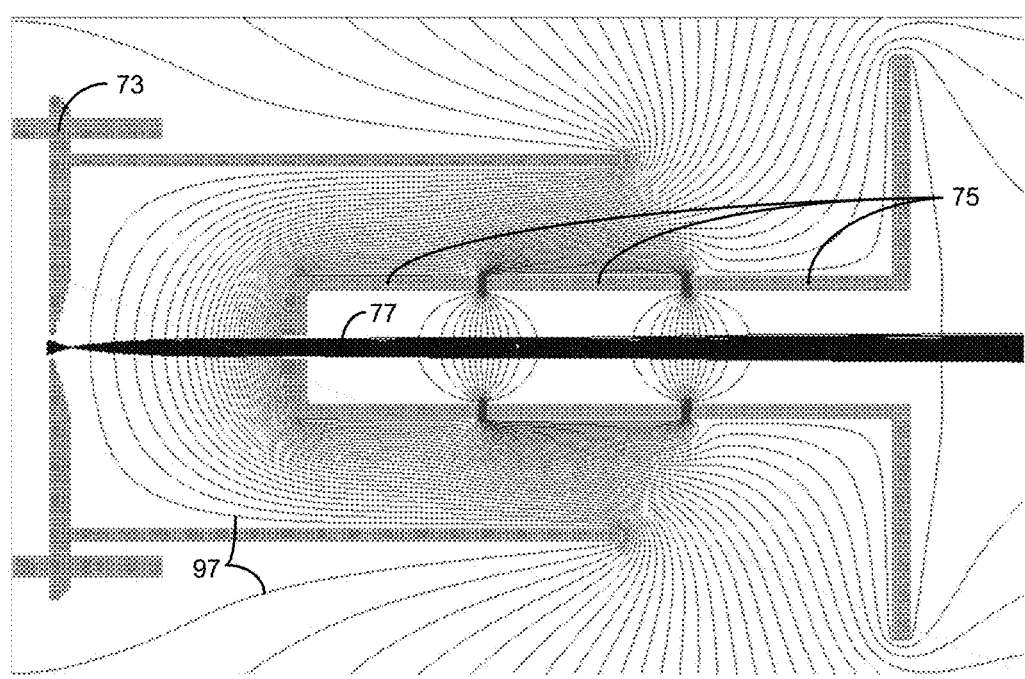
FIG. 38 is an illustration showing the ion beam extraction structure and voltage equipotential contours 97 around the three electrodes of an einzel lens 75 used to focus the ion beam 77 from the ECR ion source 82 en route to the beam chamber.

Additional illustrations of embodiments of the ECR ion source 82 and the einzel lens triplet 75 are provided in FIGS. 36-38. As shown in FIG. 38, ions pass from the ECR ion source 82 through an extraction aperture in the ion focus 73, across an extraction gap and then through the einzel triplet lens 75. While the electrode sequence of a typical einzel lens 75 has a (1) negative, (2) positive, (3) negative charge sequence, as shown in FIG. 38, the einzel lens 75 used here has a sequence of three ring-shaped electrodes with a sequence of (1) positive, (2) negative, (3) positive charge. Accordingly, the positive charge on the first electrode can be increased to shut down the flow of positive ions from the ECR ion source 82. The bent tip of first electrode in the einzel lens triplet 75 of FIG. 37 makes the ion beam convergent. As shown in FIG. 38, the electric field is perpendicular to the voltage contours 97 across the electrodes. The ions 77 decelerate when crossing the first gap between electrodes and then accelerate across the next gap. The periodic focusing structure 89, shown in FIGS. 36 and 37, is formed of permanent quadrupole magnets that maintain the uniform profile of the ion beam.

Also shown in FIG. 36 is a section of iron 113 for central field shaping and an intercepting beam collector 114 that flips in and out of the ion (e.g., H$^+$) beam to monitor and adjust the ion beam current injected into the cyclotron. The illustration of FIG. 36 also shows a microwave injection waveguide of the microwave source 70 but not the microwave power supply. Further, the illustration of FIG. 36 shows the hydrogen gas feed conduit of the hydrogen gas source 69 but not the tank or other reservoir of hydrogen gas.

In an alternative embodiment, a metal screen can be provided across the plasma chamber 71 near its base. The metal screen can block the microwaves and, thereby prevent formation of the plasma below the screen. In this embodiment, negative ions can pass through the injector column 84 in the z-axis direction along the central axis 28 and into the beam chamber 24 for isochronous acceleration. At the center of the beam chamber 24, the ions are redirected into a trajectory along the x-y plane by a pair of spiral inflector 78 provided with opposite electrical charges (e.g., via a respective voltage source coupled with each) to accelerate in an outwardly expanding spiral across the median acceleration plane 26.

Radial support links 68 and axial support links 66 pass through the outer section 88 of the cryostat 56 and are coupled with mounts 92 (shown in FIG. 9) in the bobbin 11 to maintain the bobbin 11 and the contained magnet structures in a fixed position. The support links 66 and 68 can be formed of a composite (e.g., a fiberglass/epoxy composite or a carbon-fiber/epoxy composite) that is under compression radially and in tension longitudinally (along the long axis of the support link 66/68). The support links 66 and 68 are secured flushly into mounting cups 92 on each end with cyanoacrylate adhesive (commercially available as SUPER GLUE adhesive from Super Glue Corp. of Ontario, Canada). The radial support links 68 are coupled with the primary coils 30 and 32 and bobbin 11 in a configuration whereby the radial support links 68 can provide an outward hoop force on the bobbin 11 (in the x/y plane) at a plurality of points so as to place the bobbin 11 under radial outward tension and keep the primary coils 30 and 32 centered (i.e., substantially symmetrical) about the central axis 28. As such, the radial support links 68 provide radial support against magnetic de-centering forces, whereby the cold mass approaching the iron on one side sees an exponentially increasing force and moves even closer to the iron. The radial support links 68 can comprise two or more elastic tension bands with rounded ends joined by linear segments (e.g., in the approximate shape of a conventional race or running track) and with a right circular cross-section. The bands are formed, e.g., of spiral wound glass or carbon tape impregnated with epoxy and are designed to minimize heat transfer from the high-temperature outer frame of the cyclotron 85 to the low-temperature primary coils 30 and 32. An outward force can be applied to the radial support links 68 to apply additional tension at any of the radial supports links 68 to maintain centering as various de-centering forces act on the primary coils 30 and 32. Suitable support links are described in U.S. Pat. No. 7,656,258 B1 and are referenced therein as "tension links".

Similarly, axial support links 66 can be attached to the bobbin 11 along axes parallel to the z-axis to counter an axial magnetic decentering force in order to maintain the position of the primary coils 30 and 32 symmetrically about the median acceleration plane 26 and to counterbalance attractive forces between the primary coils 30 and 32. The set of axial and radial support links 66 and 68 support the mass of the primary coils 30 and 32 and bobbin 11 against gravity in addition to providing the required centering force. As shown in FIGS. 8-12, the bobbin 11 surrounds and is flush with both the primary coil 30/32 and with the non-magnetic external reinforcement structure 62 to provide mechanical support and containment.

In operation, an electron cyclotron resonance (ECR) ion source 82 generates ions (e.g., protons) by introducing microwave energy (at a frequency, e.g, of 10 GHz) from a microwave source 70 and a gas (e.g., hydrogen) source 69 into a chamber to produce a plasma with a positive charge around the outside of the chamber for producing protons. The chamber includes an aperture 79 at its base through which the protons can escape. The escaped ions are injected from the ECR ion source 82 along the central axis 28 across an extraction gap and are then focused by an einzel lens triplet 75. After passing through the einzel lens triplet 75, the ions pass through a restriction aperture 76, and the ions' path is then bent orthogonally into the acceleration plane by spiral inflector electrodes 78 into the median acceleration plane 26, as shown in FIG. 4. The ions are then accelerated by the RF voltages applied to the electrode dees 42 in the beam chamber 24. Voltage is delivered to the primary coils 30 and 32 and to the flutter coils 21 to generate the magnetic field for isochronous acceleration of the ion in an outward spiral across the beam chamber 24 to an outer radius where the ion is extracted from the chamber 24. As shown in FIG. 10, the voltage is delivered to the flutter coils 21 via current leads 34 electrically connected, respectively, with the anode and cathode of a voltage source. The voltage is circulated through the flutter coils 21 in series via superconducting cold buses 36 that form electrical pathways between the flutter coils 21.

The electrical current leads 34 extend (e.g., as copper wires) from the voltage source through electrically insulated seals in the cryostat 56 and pass through the vacuum chamber inside the cryostat 56 through the intermediate thermal shield 54, which is thermally coupled with the first stage 50 of the cryocooler 38 (e.g., at ~40K) and then, in the form of high-temperature superconducting leads formed, e.g., of bismuth strontium calcium copper oxide (BSCCO), yttrium barium copper oxide (YBCO) or $MgB_2$ to the flutter coils 21. Additional electrical current leads 34 likewise couple a voltage source with the superconducting primary coils 30 and 32. The electrical current leads 34 can extend alongside the cryocoolers 38 through the yoke 10.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims, where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A cryogenic magnet structure, comprising:
    at least two superconducting coils that are substantially symmetric about a central axis, wherein the superconducting coils are on opposite sides of a median plane;
    a magnetic yoke surrounding the superconducting coils and containing at least a portion of a chamber, wherein the median plane extends through the chamber;
    a first cryostat containing a first of the superconducting coils; and
    a second cryostat containing a second of the superconducting coils, wherein the second cryostat is distinct from the first cryostat, and wherein the first and second cryostats are on opposite sides of the median plane in the chamber.

2. The cryogenic magnet structure of claim 1, wherein the magnetic yoke is outside the cryostats.

3. The cryogenic magnet structure of claim 1, further comprising at least one cryogenic refrigerator thermally coupled with the superconducting coils.

4. The cryogenic magnet structure of claim 3, further comprising an integral maintenance boot assembly that separates the cryogenic refrigerator from the superconducting coils to which it is thermally coupled and that is configured to preserve a vacuum in the cryostats when the cryogenic refrigerator is removed.

5. The cryogenic magnet structure of claim 1, wherein the magnet structure is a cyclotron.

6. The cryogenic magnet structure of claim 5, wherein the cyclotron has a mass less than 35 tons.

7. The cryogenic magnet structure of claim 5, further comprising:
    a plurality of superconducting flutter coils on each side of the median acceleration plane, wherein each superconducting flutter coil or pair of superconducting flutter coils serves as a sector pole tip with valleys between the sector pole tips on each side of the median acceleration plane, and wherein the sector pole tips are radially separated across the median acceleration plane by a gap that is narrower than a non-magnetic gap that separates the valleys across the median acceleration plane;
    a non-magnetic external reinforcement structure filling the valleys between the superconducting flutter coils so as to maintain the positioning of the superconducting flutter coils; and
    internal reinforcement structures mounted inside the superconducting flutter coils.

8. The cryogenic magnet structure of claim 7, wherein the flutter coils on each side of the median acceleration plane are contained in the respective cryostats.

9. The cryogenic magnet structure of claim 1, further comprising a voltage source coupled with the superconducting coils to deliver electrical current there through.

10. The cryogenic magnet structure of claim 1, further comprising:
    a first axial support link coupled with the first superconducting coil, wherein the first axial support link is configured to provide a countering force parallel to the central axis to counter an axial magnetic decentering force on the first superconducting coil; and
    a second axial support link coupled with the second superconducting coil, wherein the second axial support link is configured to provide a countering force parallel to the central axis and opposite to the countering force provided by the first axial support link to counter an axial magnetic decentering force on the second superconducting coil.

11. A method for generating a magnetic field for steering an ion beam, comprising:
    cooling at least two superconducting primary coils that are substantially symmetric about a central axis and on opposite sides of a median plane to a temperature at least as low as their superconducting transition temperature, wherein the superconducting coils are surrounded by a magnetic yoke;
    maintaining the cooled temperature of a first of the superconducting coils with a first cryostat in which the first superconducting coil is contained;
    maintaining the cooled temperature of a second of the superconducting coils with a second cryostat in which the second superconducting coil is contained;

providing a voltage to the cooled superconducting coils to generate a superconducting current in the superconducting coils; and directing an ion beam across the median plane and steering the path of the ion beam with a magnetic field generated by the superconducting coils and the magnetic yoke.

12. The method of claim 11, wherein the superconducting coils and the magnetic yoke are components of a cyclotron, the method further comprising:

introducing the ion beam in the median plane at an inner radius proximate the central axis;

accelerating the ion beam in an outward spiral from the inner radius; and extracting the ion beam from an outer radius after the acceleration.

13. The method of claim 12, wherein the accelerated ions reach an energy of 10-250 megaelectron volts (MeV).

14. The method of claim 12, wherein the magnetic yoke is maintained at a temperature over 200 Kelvin (K) as the ion beam is accelerated.

15. The method of claim 12, further comprising directing the beam of extracted ions at a tumor in a human patient.

16. The method of claim 15, wherein the beam of extracted ions is scanned across the tumor via pencil beam scanning.

17. The method of claim 11, wherein the ion beam is introduced into the median acceleration plane by injecting the ion beam from an external electron cyclotron resonance ion source.

18. The method of claim 11, wherein the extracted ions in the beam are protons with an energy of at least 220 megaelectron volts (MeV).

19. The method of claim 11, wherein the superconducting coils, the magnetic yoke, and the cryostats are included in an isochronous cyclotron, and wherein the isochronous cyclotron generates a central magnetic field in the median acceleration plane greater than 3.5 Tesla (T).

20. The method of claim 11, wherein the ion beam is directed across the median plane in a beam chamber maintained at a temperature between 10° Celsius (C) and 30° Celsius (C) between the first and second cryostats.

* * * * *